United States Patent
Long et al.

(10) Patent No.: US 7,226,574 B2
(45) Date of Patent: Jun. 5, 2007

(54) OXIDATION PROCESS USING MICROCHANNEL TECHNOLOGY AND NOVEL CATALYST USEFUL IN SAME

(75) Inventors: Richard Q. Long, New Albany, OH (US); Anna Lee Tonkovich, Dublin, OH (US); Eric Daymo, Dublin, OH (US); Barry L. Yang, Dublin, OH (US); Yong Wang, Richland, WA (US); Francis P. Daly, Delaware, OH (US)

(73) Assignee: Velocys, Inc., Plain City, OH (US)

( * ) Notice: Subject to any disclaimer, the term of this patent is extended or adjusted under 35 U.S.C. 154(b) by 415 days.

(21) Appl. No.: 10/449,913

(22) Filed: May 30, 2003

(65) Prior Publication Data
US 2004/0229752 A1 Nov. 18, 2004

Related U.S. Application Data

(63) Continuation-in-part of application No. 10/440,053, filed on May 16, 2003.

(51) Int. Cl.
*C01B 3/02* (2006.01)
*C01B 31/18* (2006.01)

(52) U.S. Cl. .................. 423/650; 423/651; 423/652; 423/653; 423/654; 423/418.2; 252/373

(58) Field of Classification Search .................. 431/2; 252/373; 423/650, 651, 652, 653, 654, 418.2, 423/437.1
See application file for complete search history.

(56) References Cited

U.S. PATENT DOCUMENTS

| | | | |
|---|---|---|---|
| 4,392,362 A | 7/1983 | Little | 62/514 |
| 4,516,632 A | 5/1985 | Swift et al. | 165/167 |
| 4,844,837 A | 7/1989 | Heck et al. | 252/373 |
| 5,309,637 A | 5/1994 | Moriarty | 29/890.054 |
| 5,317,805 A | 6/1994 | Hoopman et al. | 29/890.03 |
| 5,399,537 A | 3/1995 | Bhattacharyya et al. | 502/84 |
| 5,611,214 A | 3/1997 | Wegeng et al. | 62/498 |
| 5,648,582 A | 7/1997 | Schmidt et al. | 585/652 |
| 5,727,618 A | 3/1998 | Mundinger et al. | 165/80.4 |
| 5,811,062 A | 9/1998 | Wegeng et al. | 422/129 |
| 5,858,314 A | 1/1999 | Hsu et al. | 422/211 |
| 6,126,723 A | 10/2000 | Drost et al. | 96/4 |
| 6,129,973 A | 10/2000 | Martin et al. | 428/166 |
| 6,192,596 B1 | 2/2001 | Bennett et al. | 34/76 |
| 6,200,536 B1 | 3/2001 | Tonkovich et al. | 422/177 |
| 6,216,343 B1 | 4/2001 | Leland et al. | 29/890.032 |
| 6,220,497 B1 | 4/2001 | Benz et al. | 228/118 |
| 6,230,408 B1 | 5/2001 | Ehrfeld et al. | 29/890.039 |
| 6,313,393 B1 | 11/2001 | Drost | 136/201 |
| 6,352,577 B1 | 3/2002 | Martin et al. | 96/4 |
| 6,381,846 B2 | 5/2002 | Insley et al. | 29/890.039 |
| 6,409,940 B1 | 6/2002 | Gaffney et al. | 252/373 |
| 6,415,860 B1 | 7/2002 | Kelly et al. | 165/748 |
| 6,488,838 B1 | 12/2002 | Tonkovich et al. | 208/108 |
| 6,540,975 B2 | 4/2003 | Tonkovich et al. | 423/659 |
| 6,675,875 B1 | 1/2004 | Vafai et al. | 165/80.4 |
| 6,746,651 B1 | 6/2004 | Ponzo et al. | 422/220 |
| 6,746,819 B1 | 6/2004 | Schmitz et al. | 430/272.1 |
| 6,747,178 B1 | 6/2004 | Harston et al. | 570/175 |
| 6,749,814 B1 | 6/2004 | Bergh et al. | 422/130 |
| 6,749,817 B1 | 6/2004 | Mulvaney, III | 422/200 |
| 6,755,211 B1 | 6/2004 | O'Connor et al. | 137/554 |
| 6,756,340 B2 | 6/2004 | Voskoboynikov et al. | 502/328 |
| 6,756,515 B2 | 6/2004 | Rende et al. | 585/444 |
| 6,764,660 B1 | 7/2004 | Wiede, Jr. et al. | 422/198 |
| 6,769,444 B2 | 8/2004 | Guzman et al. | 137/15.01 |
| 6,770,245 B2 | 8/2004 | Akporiaye et al. | 422/82.12 |
| 6,773,684 B2 | 8/2004 | Lesieur et al. | 422/198 |
| 6,946,113 B2 * | 9/2005 | Seaba et al. | 423/648.1 |
| 2001/0018140 A1 | 8/2001 | Hermann et al. | 429/20 |
| 2002/0004450 A1 | 1/2002 | Gaffney et al. | 502/256 |
| 2002/0012624 A1 | 1/2002 | Figueroa et al. | 423/418.2 |

(Continued)

FOREIGN PATENT DOCUMENTS

EP      0 540 228 A1    5/1993

(Continued)

OTHER PUBLICATIONS

Anna Lee Y. Tonkovich et al. "The Catalytic Partial Oxidation of Methane in a Microchannel Chemical Reactor", Proceedings of the Second International Conference of Microreaction Technology, Mar. 1998, New Orleans, Louisiana.*

Matlosz et al.; "Microreactors as Tools in Chemical Research"; Microreaction Technology; IMRET 5: Proceedings of the Fifth International Conference on Microreaction Technology. (May 27-30, 2001).

Srinivasn et al.; "Micromachined Reactors for Catalytic Partial Oxidation Reactions"; AIChE Journal; Nov. 1997; vol. 43, No. 11; pp. 3059-3069.

(Continued)

*Primary Examiner*—Timothy C. Vanoy
(74) *Attorney, Agent, or Firm*—Renner, Otto, Boissell & Sklar, LLP

(57) ABSTRACT

A process is disclosed for converting a hydrocarbon reactant to a product comprising CO and $H_2$. The process comprises: (A) flowing a reactant composition comprising the hydrocarbon reactant and oxygen or a source of oxygen through a microchannel reactor in contact with a catalyst under reaction conditions to form the product, the microchannel reactor comprising at least one process microchannel with the catalyst positioned within the process microchannel, the hydrocarbon reactant comprising methane, the contact time for the reactant composition within the process microchannel being up to about 500 milliseconds, the temperature of the reactant composition and product within the process microchannel being up to about 1150° C., the conversion of the hydrocarbon reactant to carbon oxide being at least about 50%. The product formed in step (A) may be converted to a product comprising $CO_2$ and $H_2O$ in a microchannel reactor.

76 Claims, 5 Drawing Sheets

U.S. PATENT DOCUMENTS

| | | | |
|---|---|---|---|
| 2002/0031471 A1* | 3/2002 | Tonkovich et al. | 423/652 |
| 2002/0115730 A1 | 8/2002 | Allison et al. | 518/703 |
| 2003/0031613 A1 | 2/2003 | Tonkovich et al. | 422/211 |
| 2003/0180216 A1* | 9/2003 | TeGrotenhuis et al. | 423/659 |
| 2004/0104010 A1 | 6/2004 | Kenny et al. | 165/80.4 |
| 2004/0105812 A1* | 6/2004 | Tonkovich et al. | 423/650 |
| 2004/0107831 A1 | 6/2004 | Graham et al. | 95/96 |
| 2004/0123626 A1 | 7/2004 | Caze et al. | 65/17.2 |
| 2004/0125689 A1 | 7/2004 | Ehrfeld et al. | 366/165.1 |
| 2004/0127352 A1 | 7/2004 | Jin et al. | 502/322 |
| 2004/0130057 A1 | 7/2004 | Mehrabi et al. | 264/171.13 |
| 2004/0131345 A1 | 7/2004 | Kylberg et al. | 392/465 |
| 2004/0131507 A1 | 7/2004 | Saitmacher et al. | 422/111 |
| 2004/0131829 A1 | 7/2004 | Joseph et al. | 428/166 |
| 2004/0132832 A1 | 7/2004 | Espinoza et al. | 518/716 |
| 2004/0136902 A1 | 7/2004 | Plath et al. | 423/651 |
| 2004/0141893 A1 | 7/2004 | Martin | 422/198 |
| 2004/0143059 A1 | 7/2004 | Cabrera | 524/800 |
| 2004/0144421 A1 | 7/2004 | Parce et al. | 137/14 |
| 2004/0156762 A1 | 8/2004 | Schuppich et al. | 422/191 |
| 2005/0048333 A1* | 3/2005 | Pettit | 429/20 |
| 2005/0112047 A1* | 5/2005 | Allison et al. | 423/418.2 |

FOREIGN PATENT DOCUMENTS

| | | |
|---|---|---|
| EP | 0 584 887 A2 | 3/1994 |
| EP | 0 640 561 A1 | 3/1995 |
| EP | 0 725 038 A1 | 8/1996 |
| EP | 0 741 107 A2 | 11/1996 |
| EP | 0 940 176 A2 | 9/1999 |
| EP | 1 311 341 B1 | 8/2001 |
| EP | 0 904 608 B1 | 12/2001 |
| EP | 1 232 790 A1 | 8/2002 |
| EP | 1 382 382 A1 | 7/2003 |
| EP | 1 533 030 A1 | 5/2005 |
| FR | 2 826 293 | 12/2002 |
| WO | 97/32687 | 9/1997 |
| WO | 98/55812 | 12/1998 |
| WO | 99/48805 | 9/1999 |
| WO | 00/06295 | 2/2000 |
| WO | 01/10773 A1 | 2/2001 |
| WO | 01/12312 A2 | 2/2001 |
| WO | 01/54807 A1 | 8/2001 |
| WO | 01/60742 A1 | 8/2001 |
| WO | 01/80992 A2 | 11/2001 |
| WO | 01/95237 A2 | 12/2001 |
| WO | 02/14854 A1 | 2/2002 |
| WO | 02/064248 A2 | 8/2002 |
| WO | 02/066403 A1 | 8/2002 |
| WO | 02/095207 A1 | 11/2002 |
| WO | 03/026788 | 4/2003 |
| WO | 03/078052 A1 | 9/2003 |
| WO | 03/106386 A2 | 12/2003 |
| WO | 2004/004896 A1 | 1/2004 |
| WO | 2004/043584 A2 | 5/2004 |
| WO | 2004/045760 | 6/2004 |
| WO | 2004/050799 | 6/2004 |
| WO | 2004/052518 | 6/2004 |
| WO | 2004/052530 | 6/2004 |
| WO | 2004/052941 | 6/2004 |
| WO | 2004/054013 | 6/2004 |
| WO | 2004/054696 | 7/2004 |
| WO | 2004/062790 | 7/2004 |
| WO | 2004/062791 | 7/2004 |
| WO | 2004/062792 | 7/2004 |
| WO | 2004/067160 | 8/2004 |
| WO | 2004/067444 | 8/2004 |
| WO | 2004/067492 | 8/2004 |
| WO | 2004/067708 | 8/2004 |

OTHER PUBLICATIONS

TeGrotenhuis et al.; Optimizing Microchannel Reactors by Trading-Off Equilibrium and Reaction Kinetics through Temperature Management; Prepared for presentation at IMRET 6—6th International Conference on Microreaction Technology; Mar. 10-14, 2002.

Wegeng et al.; "Compact Fuel Processors for Fuel Cell Powered Automobiles Based on Microchannel Technology"; Fuel Cells Bulletin No. 28; pp. 8-13.

Rostami et al.; "Flow and Heat Transfer for Gas Flowing in Microchannels: a Review"; Heat and Mass Transfer 38 (2002) 359-367.

Waku et al.; "Effects of $O_2$ Concentration on the Rate and Selectivity in Oxidative Dehydrogenation of Ethane Catalyzed by Vanadium Oxide: Implications for $O_2$ Staging and Membrane Reactors"; Ind. Eng. Chem. Res. 2003, 41, 5462-5466.

Gohring et al.; "Gas Phase Reactions in Ceramic Microreactors"; IMERT 6, 10-14, Mar. 2002, New Orleans, USA, AIChE Conference Proceedings 55-60.

Hsing et al.; "Simulation of Microchannel Chemical Reactors for Heterogeneous Partial Oxidation Reactions"; Chemical Engineering Science 55 (2000) 3-13.

Besser, Ronald S. "New Directions in Reactor Design Through Miniaturization". Sep. 13, 2002, Tulane Engineering Forum.

Ouyang et al. "Flexible Microreactor System for Chemical Research at Moderate and High Temperatures". Stevens Institute of Technology.

Partial International Search Report, Annex to Form PCT/ISA/206, International Application No. PCT/US2004/010611; dated Sep. 28, 2004.

International Search Report and Written Opinion, International Application No. PCT/US2004/010611; dated Jan. 21, 2005.

International Preliminary Report on Patentability, Application No. PCT/US2004/010611, mailed Sep. 6, 2005.

Veser et al.; "Syngas Formation by Direct Oxidation of Methane Reaction Mechanisms and New Reactor Concepts"; Catalysis Today 61 (2000) 55-64.

Basini et al.; "Catalytic Partial Oxidation of Natural Gas at Elevated Pressure and Low Residence Time"; Catalysis Today 64 (2001) 9-20.

Beretta et al.; "Oxidative Dehydration of Light Paraffins in Novel Short Contact Time Reactors. Experimental and Theoretical Investigation"; Chemical Engineering Science 56 (2001) 779-787.

Cadogan; "Short Contact Time Reactions of Large Organic Free Radicals"; Tetrahedron Report No. 199; Tetrahedron vol. 42, No. 8, pp. 2135-2165, 1986.

Emig et al.; "New Reaction Engineering Concepts for Selective Oxidation Reactions"; Topics in Catalysis, Vo. 21, No. 1-3, Oct. 2002.

Fathi et al.; "Short Contact Time Oxidation Dehydrogenation of Propane"; Catalysis Today 64 (2001) 113-120.

Fichtner et al.; "Microstructured Rhodium Catalysts for the Partial Oxidation of Methane to Syngas under Pressure"; Ind. Eng. Chem. Res. 2001, 40, 3475-3483.

Goralski et al.; "Modeling Homogeneous and Heterogeneous Chemistry in the Production of Syngas from Methane"; Chemical Engineering Science 55 (2000) 1357-1370.

Lodeng et al.; "Short Contact Time Oxidative Dehydrogenation of $C_2$ and $C_3$ Alkanes Over Noble Metal Guaze Catalysts"; Applied Catalysis A: General 187 (1999) 25-31.

Ostberg et al.; "Catalytic Partial Oxidation of Natural Gas"; Prepared for Presentation at the 2002 ALChE Spring Meeting 2002, 2nd Topical Conference on Natural Gas Utilization.

"Novel Reactor Could Help Modernize U.S. Ethylene Production"; Oxidation Olefin Reactor Office of Industrial Technologies, Energy Efficiency and Renewable Energy, U.S. Department of Energy, Sep. 2001.

Communication pursuant to Article 96(2) EPC, European Patent Application No. 04 785 469.0-2104, dated Oct. 10, 2006.

* cited by examiner

OXIDATION PROCESS USING MICROCHANNEL TECHNOLOGY AND NOVEL CATALYST USEFUL IN SAME

This application is a continuation in part of U.S. application Ser. No. 10/440,053, filed May 16, 2003, which is incorporated herein by reference.

TECHNICAL FIELD

This invention relates to an oxidation process using microchannel technology and a novel catalyst useful in the oxidation process.

BACKGROUND OF THE INVENTION

Complete combustion of methane and higher order hydrocarbons is difficult to achieve under fuel-rich conditions in microchannel reactors with relatively short contact times. The combustion is incomplete and this leads to undesirable levels of carbon monoxide and carbon deposits. The problem therefore is to find a way in which to conduct a complete combustion reaction in a microchannel reactor. This invention provides a solution to this problem.

Partial oxidation reactions typically involve reacting a hydrocarbon with oxygen in the presence of a catalyst to form hydrogen and carbon monoxide. Examples include the conversion of methane to hydrogen and carbon monoxide. A problem with these reactions is that they are exothermic and are typically conducted in fixed bed reactors where hot spots tend to form. The formation of these hot spots increases the tendency of the catalyst to deactivate. This invention provides a solution to this problem.

This invention relates to a process wherein a partial oxidation reaction or a partial oxidation reaction coupled with combustion reaction is conducted in a microchannel reactor wherein the tendency to form hot spots is reduced and selectivity to the desired product is enhanced. Reductions in these hot spots with the inventive process is believed to be due at least in part to the fact that the microchannel reactor provides enhanced heat transfer characteristics and more precise control of residence times. In one embodiment, a novel, stable and highly active partial oxidation catalyst is used in the inventive process.

With the inventive process it is possible to obtain relatively high heat and mass transfer rates and shorter contact times as compared to prior art processes wherein microchannel reactors are not used. This provides for more precise temperature control as compared to such prior art. This, in turn, leads to an increase in catalyst durability and a reduction in the formation of undesired by-products. With this process, it is possible to obtain relatively high levels of conversion of the hydrocarbon reactant and high levels of selectivity to the desired product as compared to such prior art.

SUMMARY OF THE INVENTION

This invention relates to a process for converting a hydrocarbon reactant to a product comprising CO and $H_2$, the process comprising:

(A) flowing a reactant composition comprising the hydrocarbon reactant and oxygen or a source of oxygen through a microchannel reactor in contact with a catalyst under reaction conditions to form the product, the microchannel reactor comprising at least one process microchannel with the catalyst positioned within the process microchannel, the hydrocarbon reactant comprising methane, the contact time for the reactant composition and product within the process microchannel being up to about 500 milliseconds, the temperature of the reactant composition and product within the process microchannel being up to about 1150° C., the conversion of the hydrocarbon reactant being at least about 50%.

In one embodiment of the invention, the catalyst used in step (A) is a partial oxidation catalyst, the product formed in step (A) is an intermediate product, and the process further comprises the following additional step subsequent to step (A):

(B) flowing the intermediate product formed in step (A) through a microchannel reactor in contact with a combustion catalyst under reaction conditions to form a final product comprising $CO_2$ and $H_2O$.

In one embodiment, the reactant composition further comprises $H_2O$ and the product comprises $H_2$, CO and $CO_2$.

In one embodiment, the invention relates to a catalyst comprising a composition represented by the formula $$M^1_a M^2_b M^3_c Al_d O_x$$

wherein
$M^1$ is Rh, Ni, Pd, Pt, Ru, Co or a mixture of two or more thereof;
$M^2$ is Ce, Pr, Tb or a mixture of two or more thereof;
$M^3$ is La, Ba, Zr, Mg, Ca or a mixture of two or more thereof;
a is a number in the range of about 0.0001 to about 1;
b is a number in the range of zero to about 0.9999;
c is a number in the range of about 0.0001 to about 0.9999;
d is a number in the range of about 0.0001 to about 0.9999; and
x is the number of oxygens needed to fulfill the valency requirements of the elements present;
the catalyst being coated on a substrate or supported on a foam, felt, wad or fin.

In one embodiment, the invention relates to a process for making a supported catalyst, comprising:

(A) applying a layer of $Al_2O_3$ over at least part of a support structure;

(B) calcining the treated support structure formed in step (A);

(C) applying a promoter or stabilizer to the surface of the calcined support structure formed in step (B), the promoter or stabilizer comprising La, Ba, Zr, Mg, Ca, or an oxide or nitrate thereof, or a mixture of two or more thereof;

(D) calcining the treated support structure formed in step (C);

(E) applying a catalytic metal or oxide or nitrate thereof to the surface of the calcined support structure formed in step (D), the catalytic metal comprising Rh, Ni, Pd, Pt, Ru, Co or a mixture of two or more thereof; and (F) calcining the treated support structure formed in step (E) to form the supported catalyst.

BRIEF DESCRIPTION OF THE DRAWINGS

In the annexed drawings, like parts and features have like designations.

DETAILED DESCRIPTION OF THE INVENTION

Figure 1:
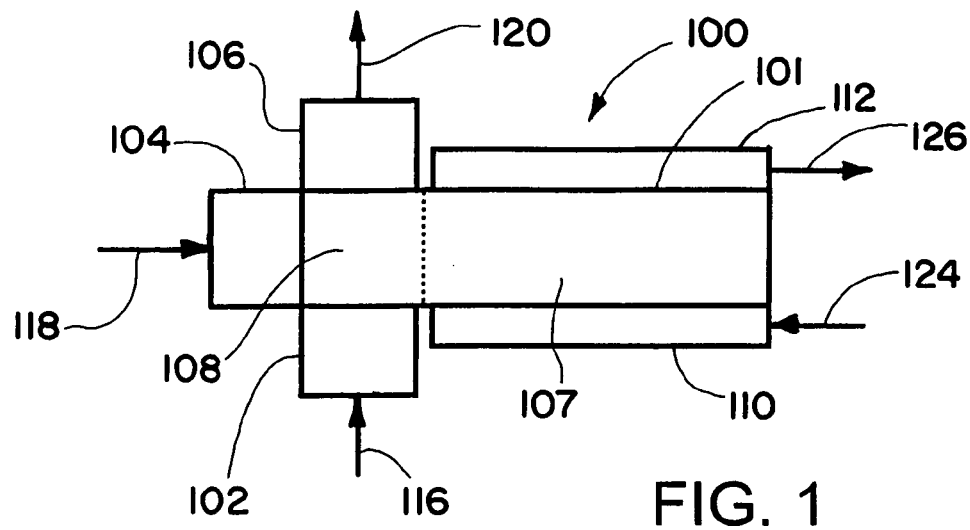
FIG. 1 is a schematic flow sheet illustrating the inventive partial oxidation process in a particular form wherein a hydrocarbon reactant and oxygen or a source of oxygen contact the inventive catalyst in a microchannel reactor and react to form a product comprising hydrogen and a carbon oxide.

The term "microchannel" refers to a channel having at least one internal dimension of height or width of up to about 10 millimeters (mm), and in one embodiment up to about 5 mm, and in one embodiment up to about 2 mm, and in one embodiment up to about 1 mm. In one embodiment, the height or width is in the range of about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.75 mm, and in one embodiment about 0.05 to about 0.5 mm. Both height and width are perpendicular to the direction of flow through the microchannel.

The term "adjacent" when referring to the position of one channel relative to the position of another channel means directly adjacent such that a wall separates the two channels. This wall may vary in thickness. However, "adjacent" channels are not separated by an intervening channel that would interfere with heat transfer between the channels.

The term "fluid" refers to a gas, a liquid, or a gas or a liquid containing dispersed solids, or a mixture thereof. The fluid may be in the form of a gas containing dispersed liquid droplets.

The term "contact time" refers to the volume of the reaction zone within the microchannel reactor divided by the volumetric feed flow rate of the reactant composition at a temperature of 0° C. and a pressure of one atmosphere.

The term "residence time" refers to the internal volume of a space (e.g., the reaction zone within a microchannel reactor) occupied by a fluid flowing through the space divided by the average volumetric flowrate for the fluid flowing through the space at the temperature and pressure being used.

The term "reaction zone" refers to the space within the microchannel reactor wherein the reactants contact the catalyst.

The term "conversion of hydrocarbon reactant" refers to the hydrocarbon reactant mole change between the reactant composition and the product divided by the moles of the hydrocarbon reactant in the reactant composition.

The term "selectivity to desired product" refers to the moles of the desired oxygenate or nitrile produced divided by the moles of the desired oxygenate or nitrile produced plus moles of other products (e.g., CO, $CO_2$) produced multiplied by their respective stoichiometric factors. For example, for the oxidation of ethylene to ethylene oxide with carbon dioxide as an unwanted side product, the production of one mole of ethylene oxide and one mole of carbon dioxide would correspond to a selectivity of $100\times(1/(1+0.5))$ =67%.

The term "hydrocarbon" denotes a compound having a hydrocarbon or predominantly hydrocarbon character. These hydrocarbon compounds include the following:

(1) Purely hydrocarbon compounds; that is, aliphatic compounds, (e.g., alkane or alkylene), alicyclic compounds (e.g., cycloalkane, cycloalkylene), aromatic compounds, aliphatic- and alicyclic-substituted aromatic compounds, aromatic-substituted aliphatic compounds and aromatic-substituted alicyclic compounds, and the like. Examples include methane, ethane, ethylene, propane, propylene, ethyl cyclohexane, toluene, the xylenes, ethyl benzene, styrene, etc.

(2) Substituted hydrocarbon compounds; that is, hydrocarbon compound containing non-hydrocarbon substituents which do not alter the predominantly hydrocarbon character of the compound. Examples of the non-hydrocarbon substituents include hydroxy, acyl, nitro, etc.

(3) Hetero substituted hydrocarbon compounds; that is, hydrocarbon compounds which, while predominantly hydrocarbon in character, contain atoms other than carbon in a chain or ring otherwise composed of carbon atoms. Suitable hetero atoms include, for example, nitrogen, oxygen and sulfur.

Figure 2:
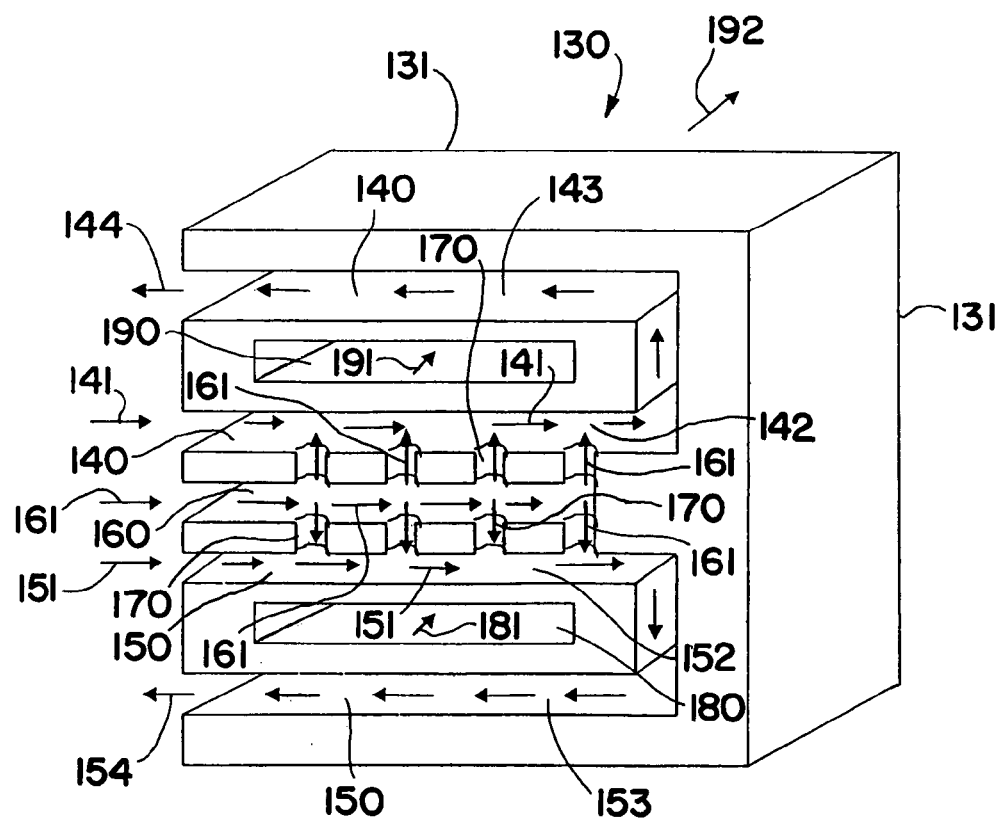
FIG. 2 is a schematic flow sheet illustrating the operation of a particular form of a microchannel reactor used with the inventive partial oxidation process.

The inventive process may be conducted as illustrated in FIGS. 1 and 2. Referring to FIG. 1, the process is operated using microchannel reactor 100 which includes microchannel reactor core 101, reactant header 102, oxidant header 104, product footer 106, heat exchange header 110 and heat exchange footer 112. The microchannel reactor core 101 includes reactor zone 107, and manifold and recuperator 108. The reactant composition comprising the hydrocarbon reactant flows into the microchannel reactor 100 through the reactant header 102, as indicated by directional arrow 116. The oxygen or source of oxygen flows into the microchannel reactor 100 through the oxidant header 104 as indicated by directional arrow 118. The hydrocarbon reactant and oxygen or source of oxygen flow into and through the manifold and recuperator 108 into the reactor zone 107 wherein they contact the catalyst and react to form the desired product. The product flows from the reactor zone 107 through the manifold and recuperator 108 to product footer 106, and out of product footer 106 as indicated by directional arrow 120. A heat exchange fluid may flow into heat exchange header 110, as indicated by directional arrow 124, and from heat exchange header 110 through microchannel reactor core 101 to heat exchange footer 112, and out of heat exchange footer 112, as indicated by directional arrow 126. The reactants may be preheated prior to entering the reactor zone. The hydrocarbon reactant and the oxygen or source of oxygen may be mixed prior to entering the reactor zone, or they may be mixed in the reactor zone.

Within the microchannel reactor core 101, the oxygen or source of oxygen may be added to the hydrocarbon reactant using staged addition. This is shown in FIG. 2 which illustrates repeating unit 130, which is used in the microchannel reactor 100 illustrated in FIG. 1. Repeating unit 130 is housed within housing unit 131 and includes process microchannels 140 and 150, oxidant microchannel 160, orifices 170, and heat exchange microchannels 180 and 190. The hydrocarbon reactant flows through process microchannels 140 and 150, as indicated by the directional arrows 141 and 151, respectively. Oxygen or a source of oxygen flows through oxidant microchannel 160 into orifices 170, as indicated by directional arrows 161. The oxygen or oxygen source mixes with the hydrocarbon reactant in the process microchannels 140 and 150. The process microchannels 140 and 150 have reaction zones 142 and 152, respectively, wherein the catalyst is present and the reactants contact the catalyst and undergo reaction to form the desired product, and channel zones 143 and 153, respectively, wherein further contact with the foregoing catalyst or a different catalyst may be effected, or product cooling and/or quenching may be effected. The catalyst positioned in the reaction zone is a partial oxidation catalyst. In one embodiment, a combustion catalyst may be positioned downstream of the partial oxidation catalyst in the reaction zones 142 and 152 and/or in the channel zones 143 and 153. The product exits the process microchannels 140 and 150, as indicated by the directional arrows 144 and 154, respectively. The product exiting the process microchannels 140 and 150 flows to the manifold and recuperator 108, and from the manifold and recuperator 108 through the product footer 106 as indicated by directional arrow 120. Heat exchange fluid flows from header 110 through heat exchange channels 180 and 190, as indicated by directional arrows 181, and 191 and 192, respectively, to heat exchange footer 112. The heat exchange channels 180 and 190 are aligned to provide a flow in a cross-current direction relative to the process microchannels 140 and 150 as indicated by arrows 181, 191 and 192. The process microchannels 140 and 150 transfer heat to the heat exchange channels. The heat exchange fluid may be recirculated using known techniques. Alternatively, the heat exchange channels may be oriented to provide for flow of the heat exchange fluid in a cocurrent or counter current direction relative to the direction of the flow of fluid through the process microchannels 140 and 150. The repeating unit 130 illustrated in FIG. 2 may occur once within the microchannel reactor 100 or it may be repeated any number of times, for example, two, three, four, five, ten, twenty, fifty, one hundred, hundreds, one thousand, thousands, ten thousand, tens of thousands, one hundred thousand, hundreds of thousands or millions of times. The staged oxygen addition provided for in this process provides the advantage of lowering local oxygen pressure and favoring desired lower-order partial oxidation reactions over higher-order competing and undesired combustion reactions.

Each of the process microchannels 140 and 150 and the oxidant microchannel 160 may have at least one internal dimension of height or width of up to about 10 mm, and in one embodiment from about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.5 mm. The other internal dimension of height or width may be of any value, for example, it may range from about 0.1 cm to about 100 cm, and in one embodiment from about 0.1 to about 75 cm, and in one embodiment from about 0.1 to about 50 cm, and in one embodiment about 0.2 cm to about 25 cm. The length of each of the process microchannels 140 and 250, and the oxidant microchannel 160, may be of any value, for example, the lengths may range from about 1 cm to about 500 cm, and in one embodiment 1 cm to about 250 cm, and in one embodiment 1 cm to about 100 cm, and in one embodiment 1 cm to about 50 cm, and in one embodiment about 2 to about 25 cm.

Each of the heat exchange channels 180 and 190 may have at least one internal dimension of height or width of up to about 10 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. The other internal dimension may range from about 1 mm to about 1 m, and in one embodiment about 1 mm to about 0.5 m, and in one embodiment about 2 mm to about 10 cm. The length of the heat exchange channels may range from about 1 mm to about 1 m, and in one embodiment about 1 cm to about 0.5 m. These heat exchange channels may be microchannels. The separation between each process microchannel 140 or 150 and the next adjacent heat exchange channel 180 or 190 may range from about 0.05 mm to about 5 mm, and in one embodiment about 0.2 mm to about 2 mm.

The microchannel reactor 100 may be made using known techniques. These include laminating interleaved shims, where shims designed for the process microchannels, oxidant microchannels and heat exchange channels are interleaved.

The housing 131, process microchannels 140 and 150, oxidant microchannel 160, and heat exchange channels 180 and 190 may be made of any material that provides sufficient strength, dimensional stability and heat transfer characteristics to permit operation of the inventive process. These materials include steel (e.g., stainless steel, carbon steel, and the like); monel; inconel; aluminum, titanium; nickel, platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof.

Alternatively, the staged addition of the oxygen or source of oxygen to the microchannel reactor may be effected using separate devices, through the use of small orifices or jets within one device, or from a microporous membrane or alternate sparging sheet. The staged addition of oxygen to partial oxidation reactions, and specifically oxidative dehydrogenation reactions, is disclosed in Tonkovich, Zilka, Jimenz, Roberts, and Cox, 1996, "Experimental Investigations of Inorganic Membrane Reactors: a Distributed Feed Approach for Partial Oxidation Reactions," Chemical Engineering Science, 51(5), 789–806), which is incorporated herein by reference.

In one embodiment, the process microchannels 140 and 150 may contain a bulk flow path. The term "bulk flow path" refers to an open path (contiguous bulk flow region) within the process microchannels. A contiguous bulk flow region allows rapid fluid flow through the microchannels without large pressure drops. In one embodiment, the flow of fluid in the bulk flow region is laminar. Bulk flow regions within each process microchannel may have a cross-sectional area of about 0.05 to about 10,000 $mm^2$, and in one embodiment about 0.05 to about 5000 $mm^2$, and in one embodiment about 0.1 to about 2500 mm², and in one embodiment about 0.2 to about 1000 mm², and in one embodiment about 0.3 to about 500 mm², and in one embodiment about 0.4 to about 250 mm², and in one embodiment about 0.5 to about 125 mm². The bulk flow regions may comprise from about 5% to about 95%, and in one embodiment about 30% to about 80% of the cross-section of the process microchannels 140 and 150.

The reactant composition may be in the form of a fluid. This fluid may be a liquid or a gas, and in one embodiment it is in the form of a gas. This fluid may be in the form of a gas containing dispersed liquid droplets. The reactant composition comprises methane and may further comprise one or more additional hydrocarbon reactants. The concentration of methane in the mixture of methane and one or more additional hydrocarbon reactants may range up to about 100% methane, and in one embodiment from about 10 to about 90% by volume methane, and in one embodiment about 50 to about 90% by volume methane.

The purity of the reactant composition is not critical, though it is desirable to avoid the presence of compounds which may poison the catalyst. As a result, the reactant composition may further comprise impurities such as air, carbon dioxide, and the like.

The reactant composition may include a diluent material. Examples of such diluents include nitrogen, helium, carbon dioxide, liquid water, steam, and the like. The volume ratio of diluent to hydrocarbon reactant in the reactant composition may range from zero to about 80% by volume, and in one embodiment from zero to about 50% by volume. However, an advantage of at least one embodiment of the invention is that it is possible to conduct the inventive process without the use of such diluents, thus a more efficient and compact process may be provided.

The hydrocarbon reactant comprises methane and may further comprise one or more additional hydrocarbon compounds that are capable of undergoing an oxidation reaction, and are a fluid (and in one embodiment a vapor) at the temperature and pressure used within the process microchannels. Examples include saturated aliphatic compounds (e.g., alkanes), unsaturated aliphatic compounds (e.g., monoenes, polyenes, and the like), alkyl substituted aromatic compounds, alkylene substituted aromatic compounds, oils, normally liquid fuels, and the like.

The saturated aliphatic compounds include alkanes containing 2 to about 20 carbon atoms per molecule, and in one embodiment 2 to about 18 carbon atoms, and in one embodiment 2 to about 16 carbon atoms, and in one embodiment 2 to about 14 carbon atoms, and in one embodiment 2 to about 12 carbon atoms, and in one embodiment 2 to about 10 carbon atoms, and in one embodiment 2 to about 8 carbon atoms, and in one embodiment 2 to about 6 carbon atoms, and in one embodiment 2 to about 4 carbon atoms. These include ethane, propane, isopropane, butane, isobutane, the pentanes, the hexanes, the heptanes, the octanes, the nonanes, the decanes, and the like.

The unsaturated aliphatic compounds include alkenes or alkylenes containing 2 to about 20 carbon atoms, and in one embodiment 2 to about 18 carbon atoms, and in one embodiment 2 to about 16 carbon atoms, and in one embodiment 2 to about 14 carbon atoms, and in one embodiment 2 to about 12 carbon atoms, and in one embodiment 2 to about 10 carbon atoms, and in one embodiment 2 to about 8 carbon atoms, and in one embodiment 2 to about 6 carbon atoms per molecule, and in one embodiment 2 to about 4 carbon atoms. These include ethylene; propylene; 1-butene; 2-butene; isobutylene; 1-pentene;2-pentene; 3-methyl-1-butene; 2-methyl-2-butene; 1-hexene; 2,3-dimethyl-2-butene; 1-heptene; 1-octene; 1-nonene; 1-decene; and the like.

The unsaturated aliphatic compounds may comprise polyenes. These include dienes, trienes, and the like. These compounds may contain 3 to about 20 carbon atoms per molecule, and in one embodiment 3 to about 18 carbon atoms, and in one embodiment 3 to about 16 carbon atoms, and in one embodiment 3 to about 14 carbon atoms, and in one embodiment 3 to about 12 carbon atoms, and in one embodiment 3 to about 10 carbon atoms, and in one embodiment about 4 to about 8 carbon atoms, and in one embodiment about 4 to about 6 carbon atoms. Examples include 1,2-propadiene (also known as allene); 1,3-butadiene; 2-methyl-1,3-butadiene (also known as isoprene); 1,3-pentadiene; 1,4-pentadiene; 1,5-hexadiene; 2,4-hexadiene; 2,3-dimethyl-1,3-butadiene; and the like.

The alkyl or alkylene substituted aromatic compounds may contain one or more alkyl or alkylene substituents. These compounds may be monocyclic (e.g., phenyl) or a polycyclic (e.g., naphthyl). These compounds include alkyl substituted aromatic compounds containing one or more alkyl groups containing 1 to about 20 carbon atoms, and in one embodiment 1 to about 18 carbon atoms, and in one embodiment 1 to about 16 carbon atoms, and in one embodiment 1 to about 14 carbon atoms, and in one embodiment 1 to about 12 carbon atoms, and in one embodiment 1 to about 10 carbon atoms, and in one embodiment 1 to about 8 carbon atoms, and in one embodiment about 2 to about 6 carbon atoms, and in one embodiment about 2 to about 4 carbon atoms. These also include the akylene substituted aromatic compounds containing one or more alkylene groups containing 2 to about 20 carbon atoms, and in one embodiment 2 to about 18 carbon atoms, and in one embodiment 2 to about 16 carbon atoms, and in one embodiment 2 to about 14 carbon atoms, and in one embodiment 2 to about 12 carbon atoms, and in one embodiment 2 to about 10 carbon atoms, and in one embodiment 2 to about 8 carbon atoms, and in one embodiment about 2 to about 6 carbon atoms, and in one embodiment about 2 to about 4 carbon atoms. Examples include toluene, o-xylene, m-xylene, p-xylene, hemimellitene, pseudocumene, mesitylene, prehnitene, isodurene, durene, pentamethylbenzene, hexamethylbenzene, ethylbenzene, n-propylbenzene, cumene, n-butylbenzene, isobutylbenzene, sec-butylbenzene, tert-butylbenzene, p-cymene, styrene, and the like.

The hydrocarbon reactant may further comprise a natural oil, synthetic oil or mixture thereof. The natural oils include animal oils and vegetable oils (e.g., castor oil, lard oil) as well as mineral oils such as liquid petroleum oils. Oils derived from coal or shale may be used. Synthetic oils include hydrocarbon oils such as polymerized and interpolymerized olefins, polyphenyls, alkylated diphenyl esters, alkylated diphenyl sulfides, and the like. Alkylene oxide polymers and interpolymers and derivatives thereof where the thermal hydroxyl groups have been modified by esterification, etherification, etc., constitute another class of known synthetic oils that can be used as the hydrocarbon reactant. The synthetic oils that are useful as the hydrocarbon reactant include the esters of dicarboxylic acids with a variety of alcohols. The hydrocarbon reactant may comprise a poly-alpha-olefin. The hydrocarbon reactant may comprise a Fischer-Tropsch synthesized hydrocarbon. The hydrocarbon reactant may be obtained from a process stream generated during oil refining, chemical synthesis, and the like.

The hydrocarbon reactant may further comprise a normally liquid hydrocarbon fuel. These include distillate fuels such as motor gasoline, diesel fuel or fuel oil. Hydrocarbon reactants derived from vegetable sources, mineral sources, and mixtures thereof may be used. These include hydrocarbon reactants derived from soybean, rapeseed, palm, shale, coal, tar sands, and the like.

The oxygen or oxygen source may comprise molecular oxygen, air or other oxidants, such as nitrogen oxides, which can function as a source of oxygen. The oxygen source may be carbon dioxide, carbon monoxide or a peroxide (e.g., hydrogen peroxide). Gaseous mixtures containing oxygen, such as mixtures of oxygen and air, or mixtures of oxygen and an inert gas (e.g., helium, argon, etc.) or a diluent gas (e.g., carbon dioxide, water vapor, etc.) may be used.

The mole ratio of carbon in the hydrocarbon reactant to oxygen may range from about 10:1 to about 1:1, and in one embodiment about 4:1 to about 1:1, and in one embodiment about 2.4:1 to about 1.6:1.

The heat exchange fluid may be any fluid. These include air, steam, liquid water, gaseous nitrogen, liquid nitrogen, other gases including inert gases, carbon monoxide, molten salt, oils such as mineral oil, and heat exchange fluids such as Dowtherm A and Therminol which are available from Dow-Union Carbide.

The heat exchange fluid may comprise one or more of the reactant streams. This can provide process pre-heat and increase overall thermal efficiency of the process.

In one embodiment, the heat exchange channels comprise process channels wherein an endothermic reaction is conducted. These heat exchange process channels may be microchannels. Examples of endothermic reactions that may be conducted in the heat exchange channels include steam reforming and dehydrogenation reactions. A typical heat flux for convective cooling in a microchannel reactor is on the order of about 1 to about 10 W/cm$^2$. The incorporation of a simultaneous endothermic reaction to provide an improved heat sink may enable a typical heat flux of roughly an order of magnitude above the convective cooling heat flux. The use of simultaneous exothermic and endothermic reactions to exchange heat in a microchannel reactor is disclosed in U.S. patent application Ser. No. 10/222,196, filed Aug. 15, 2002, which is incorporated herein by reference.

In one embodiment, the heat exchange fluid undergoes a phase change as it flows through the heat exchange channels. This phase change provides additional heat removal from the process microchannels beyond that provided by convective cooling. For a liquid heat exchange fluid being vaporized, the additional heat being transferred from the process microchannels would result from the latent heat of vaporization required by the heat exchange fluid. An example of such a phase change would be an oil or water that undergoes boiling.

The cooling of the process microchannels 140 and 150 during the inventive process, in one embodiment, is advantageous for controlling selectivity towards the main or desired product due to the fact that such added cooling reduces or eliminates the formation of undesired by-products from undesired parallel reactions with higher activation energies. As a result of this cooling, in one embodiment, the temperature of the reactant composition at the entrance to the process microchannels 140 and 150 may be within about 200° C., and in one embodiment within about 150° C., and in one embodiment within about 100° C., and in one embodiment within about 50° C., and in one embodiment within about 25° C., and in one embodiment within about 10° C., of the temperature of the product (or mixture of product and unreacted reactants) at the exit of the process microchannels.

The catalyst used in a microchannel reactor may have any size and geometric configuration that fits within the process microchannels. The catalyst may be in the form of particulate solids (e.g., pellets, powder, fibers, and the like) having a median particle diameter of about 1 to about 1000 µm, and in one embodiment about 10 to about 500 µm, and in one embodiment about 25 to about 250 µm. The catalyst may be supported in a porous structure such as a foam, felt, wad or a combination thereof. The term "foam" is used herein to refer to a structure with continuous walls defining pores throughout the structure. The term "felt" is used herein to refer to a structure of fibers with interstitial spaces therebetween. The term "wad" is used herein to refer to a structure of tangled strands, like steel wool. The catalyst may be supported on a honeycomb structure.

Figure 3:
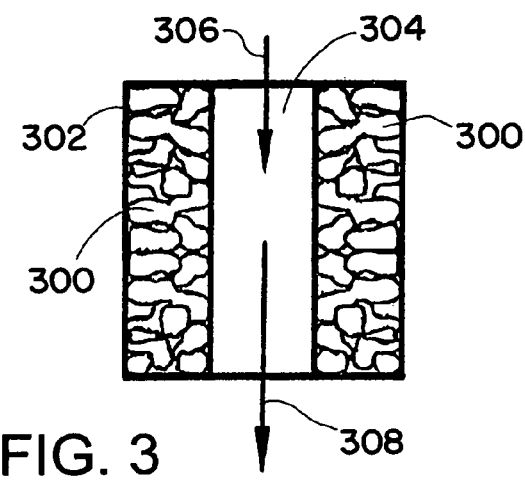
FIG. 3 is a schematic illustration of a process microchannel used with the inventive partial oxidation process, the process microchannel containing a catalyst having a flow-by configuration.

The catalyst may be in the form of a flow-by structure such as a felt with an adjacent gap, a foam with an adjacent gap, a fin structure with gaps, a washcoat on any inserted substrate, or a gauze that is parallel to the flow direction with a corresponding gap for flow. An example of a flow-by structure is illustrated in FIG. 3. In FIG. 3, the catalyst 300 is contained within process microchannel 302. An open passage way 304 permits the flow of fluid through the process microchannel 302 in contact with the catalyst 300 as indicated by arrows 306 and 308.

Figure 4:
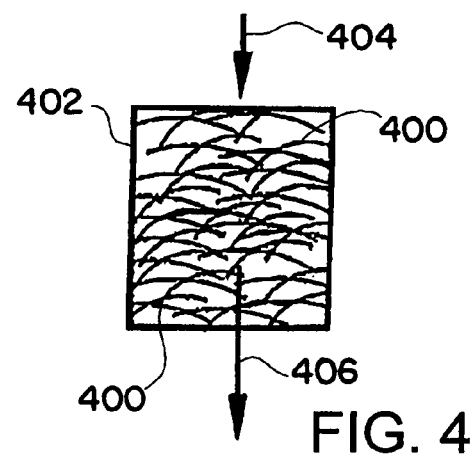
FIG. 4 is a schematic illustration of a process microchannel used with the inventive partial oxidation process, the process microchannel containing a catalyst having a flow-through configuration.

The catalyst may be in the form of a flow-through structure such as a foam, wad, pellet, powder, or gauze. An example of a flow-through structure is illustrated in FIG. 4. In FIG. 4, the flow-through catalyst 400 is contained within process microchannel 402 and the fluid flows through the catalyst 400 as indicated by arrows 404 and 406.

The catalyst may be directly washcoated on the interior walls of the process microchannels, grown on the walls from solution, or coated in situ on a fin structure. The catalyst may be in the form of a single piece of porous contiguous material, or many pieces in physical contact. In one embodiment, the catalyst is comprised of a contiguous material and has a contiguous porosity such that molecules can diffuse through the catalyst. In this embodiment, the fluids flow through the catalyst rather than around it. In one embodiment, the cross-sectional area of the catalyst occupies about 1 to about 99%, and in one embodiment about 10 to about 95% of the cross-sectional area of the process microchannels. The catalyst may have a surface area, as measured by BET, of greater than about 0.5 m$^2$/g, and in one embodiment greater than about 2 m$^2$/g.

The catalyst may comprise a porous support, an interfacial layer on the porous support, and a catalyst material on the interfacial layer. The interfacial layer may be solution deposited on the support or it may be deposited by chemical vapor deposition or physical vapor deposition. In one embodiment the catalyst has a porous support, a buffer layer, an interfacial layer, and a catalyst material. Any of the foregoing layers may be continuous or discontinuous as in the form of spots or dots, or in the form of a layer with gaps or holes.

The porous support may have a porosity of at least about 5% as measured by mercury porosimetry and an average pore size (sum of pore diameters divided by number of pores) of about 1 to about 1000 µm. The porous support may be a porous ceramic or a metal foam. Other porous supports that may be used include carbides, nitrides, and composite materials. The porous support may have a porosity of about 30% to about 99%, and in one embodiment about 60% to about 98%. The porous support may be in the form of a foam, felt, wad, or a combination thereof. The open cells of the metal foam may range from about 20 pores per inch (ppi)

to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The buffer layer, when present, may have a different composition and/or density than both the porous support and the interfacial layers, and in one embodiment has a coefficient of thermal expansion that is intermediate the thermal expansion coefficients of the porous support and the interfacial layer. The buffer layer may be a metal oxide or metal carbide. The buffer layer may be comprised of $Al_2O_3$, $TiO_2$, $SiO_2$, $ZrO_2$, or combination thereof. The $Al_2O_3$ may be $\alpha$-$Al_2O_3$, $\gamma$-$Al_2O_3$ or a combination thereof. $\alpha$-$Al_2O_3$ provides the advantage of excellent resistance to oxygen diffusion. The buffer layer may be formed of two or more compositionally different sublayers. For example, when the porous support is metal, for example a stainless steel foam, a buffer layer formed of two compositionally different sub-layers may be used. The first sublayer (in contact with the porous support) may be $TiO_2$. The second sublayer may be $\alpha$-$Al_2O_3$ which is placed upon the $TiO_2$. In one embodiment, the $\alpha$-$Al_2O_3$ sublayer is a dense layer that provides protection of the underlying metal surface. A less dense, high surface area interfacial layer such as alumina may then be deposited as support for a catalytically active layer.

The porous support may have a thermal coefficient of expansion different from that of the interfacial layer. In such a case a buffer layer may be needed to transition between the two coefficients of thermal expansion. The thermal expansion coefficient of the buffer layer can be tailored by controlling its composition to obtain an expansion coefficient that is compatible with the expansion coefficients of the porous support and interfacial layers. The buffer layer should be free of openings and pin holes to provide superior protection of the underlying support. The buffer layer may be nonporous. The buffer layer may have a thickness that is less than one half of the average pore size of the porous support. The buffer layer may have a thickness of about 0.05 to about 10 µm, and in one embodiment about 0.05 to about 5 µm.

In one embodiment of the invention, adequate adhesion and chemical stability may be obtained without a buffer layer. In this embodiment the buffer layer may be omitted.

The interfacial layer may comprise nitrides, carbides, sulfides, halides, metal oxides, carbon, or a combination thereof. The interfacial layer provides high surface area and/or provides a desirable catalyst-support interaction for supported catalysts. The interfacial layer may be comprised of any material that is conventionally used as a catalyst support. The interfacial layer may be comprised of a metal oxide. Examples of metal oxides that may be used include $\gamma$-$Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer may serve as a catalytically active layer without any further catalytically active material deposited thereon. Usually, however, the interfacial layer is used in combination with a catalytically active layer. The interfacial layer may also be formed of two or more compositionally different sublayers. The interfacial layer may have a thickness that is less than one half of the average pore size of the porous support. The interfacial layer thickness may range from about 0.5 to about 100 µm, and in one embodiment from about 1 to about 50 µm. The interfacial layer may be either crystalline or amorphous. The interfacial layer may have a BET surface area of at least about 1 $m^2/g$.

The catalyst may be deposited on the interfacial layer. Alternatively, the catalyst material may be simultaneously deposited with the interfacial layer. The catalyst layer may be intimately dispersed on the interfacial layer. That the catalyst layer is "dispersed on" or "deposited on" the interfacial layer includes the conventional understanding that microscopic catalyst particles are dispersed: on the support layer (i.e., interfacial layer) surface, in crevices in the support layer, and in open pores in the support layer.

Figure 5:
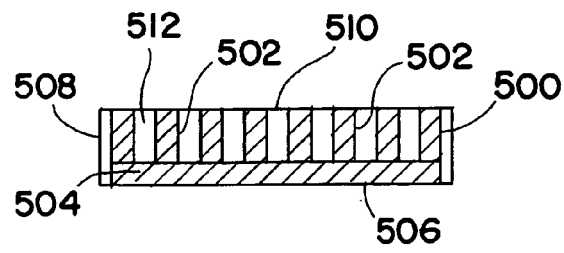
FIG. 5 is a schematic illustration of a process microchannel used in the inventive partial oxidation process, the process microchannel containing a fin assembly comprising a plurality of fins, the inventive catalyst being supported by the fins.
Figure 6:
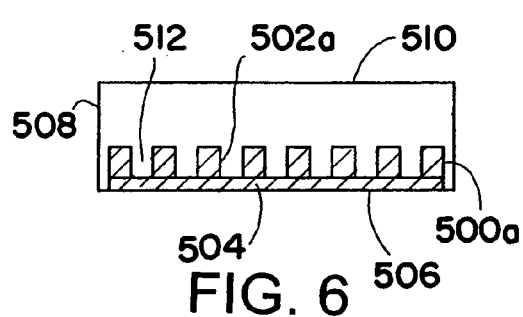
FIG. 6 illustrates an alternate embodiment of the process microchannel and fin assembly illustrated in FIG. 5.
Figure 7:
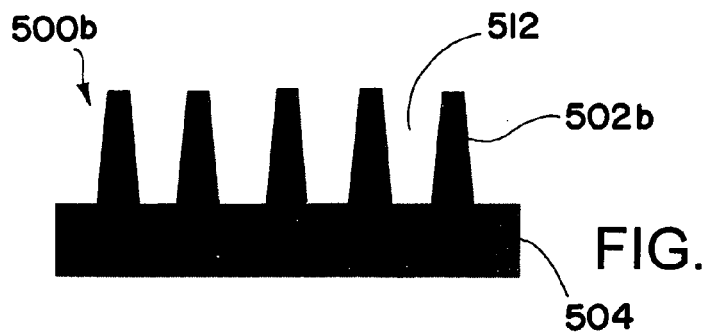
FIG. 7 illustrates an alternate embodiment of the fin assembly illustrated in FIG. 5.

The catalyst may be supported on an assembly of one or more fins which may be positioned within each of the process microchannels. Examples are illustrated in FIGS. 5–7. Referring to FIG. 5, fin assembly 500 includes fins 502 which are mounted on fin support 504 which overlies base wall 506 of process microchannel 508. The fins 502 project from the fin support 504 into the interior of the process microchannel 508. The fins 502 extend to and contact the interior surface of upper wall 510 of process microchannel 508. The fin channels 512 between the fins 502 provide passage ways for fluid to flow through the process microchannel 508 parallel to its length. Each of the fins 502 has an exterior surface on each of its sides, this exterior surface provides a support base for a catalyst. With the inventive process, the reactant composition flows through the fin channels 512, contact the catalyst supported on the exterior surface of the fins 502, and react to form a product. The fin assembly 500a illustrated in FIG. 6 is similar to the fin assembly 500 illustrated in FIG. 5 except that the fins 502a do not extend all the way to the interior surface of the upper wall 510 of the microchannel 508. The fin assembly 500b illustrated in FIG. 7 is similar to the fin assembly 500 illustrated in FIG. 5 except that the fins 502b in the fin assembly 500b have cross sectional shapes in the form of trapezoids. Each of the fins may have a height ranging from about 0.02 mm up to the height of the process microchannel 508, and in one embodiment from about 0.02 to about 10 mm, and in one embodiment from about 0.02 to about 5 mm, and in one embodiment from about 0.02 to about 2 mm. The width of each fin may range from about 0.02 to about 5 mm, and in one embodiment from about 0.02 to about 2 mm and in one embodiment about 0.02 to about 1 mm. The length of each fin may be of any length up to the length of the process microchannel 508, and in one embodiment from about 5 mm to about 500 cm, and in one embodiment about 1 cm to about 250 cm, and in one embodiment about 1 cm to about 100 cm, and in one embodiment about 2 cm to about 25 cm. The gap between each of the fins may be of any value and may range from about 0.02 to about 5 mm, and in one embodiment from about 0.02 to about 2 mm, and in one embodiment from about 0.02 to about 1 mm. The number of fins in the process microchannel 508 may range from about 1 to about 50 fins per centimeter of width of the process microchannel 508, and in one embodiment from about 1 to about 30 fins per centimeter, and in one embodiment from about 1 to about 10 fins per centimeter, and in one embodiment from about 1 to about 5 fins per centimeter, and in one embodiment from about 1 to about 3 fins per centimeter. Each of the fins may have a cross-section in the form of a rectangle or square as illustrated in FIGS. 5 and 6, or a trapezoid as illustrated in FIG. 7. When viewed along its length, each fin may be straight, tapered or have a serpentine configuration. The fins may be made of any material that provides sufficient strength, dimensional stability and heat transfer characteristics to permit operation for which the process microchannel is intended. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof. The fin may be made of an $Al_2O_3$ forming material such as an alloy comprising Fe, Cr, Al and Y, or a $Cr_2O_3$ forming material such as an alloy of Ni, Cr and Fe.

The catalyst may comprise Rh, Pt, Ni, Cr, Ru, Pd, Os, Ir, or an oxide thereof, or a mixture of two or more thereof. Partial oxidation catalysts based on one or more of the foregoing are disclosed in U.S. Pat. Nos. 5,648,582 and 6,409,940 B1; U.S. Patent Application Publications 2002/0004450 A1, 2002/0012624 A1 and 2002/0115730 A1; PCT International Publication Nos. WO 99/48805, WO 01/80992 A2 and WO 02/066403 A1; and European Patent Application Publication Nos. 0640561 A1, EP 0725038 A1 and EP 0741107 A1. These catalysts may be in any of the forms or supported on any of the support structures discussed above.

The partial oxidation catalyst may comprise platinum or an oxide thereof deposited on a ceramic support as disclosed in U.S. Pat. No. 5,648,582, which is incorporated herein by reference.

The partial oxidation catalyst may comprise nickel and rhodium, or oxides thereof, deposited on a support structure made of a spinel, a perovskite, magnesium oxide, a pyrochlore, a brownmillerite, zirconium phosphate, magnesium stabilized zirconia, zirconia stabilized alumina, silicon carbide, yttrium stabilized zirconia, calcium stabilized zirconia, yttrium aluminum garnet, alumina, cordierite, $ZrO_2$, $MgAl_2O$, $SiO_2$ or $TiO_2$. These are disclosed in U.S. Pat. No. 6,409,940 B1, which is incorporated herein by reference.

The partial oxidation catalyst may comprise a lanthanide-promoted rhodium catalyst as disclosed in U.S. Patent Publication No. 2002/0115730A1, which is incorporated herein by reference.

The partial oxidation catalyst may comprise a Ni—Cr, Ni—Co—Cr or Ni—Rh alloy as disclosed in U.S. Patent Publication No. 2002/0012624A1, which is incorporated herein by reference.

The partial oxidation catalyst may comprise rhodium, nickel, chromium, or a combination thereof supported on ceramic oxide fiber as disclosed in U.S. Patent Publication No. 2002/0004450A1, which is incorporated herein by reference.

The partial oxidation catalyst may comprise rhodium supported on a refractory oxide support as disclosed in PCT International Publication No. WO 99/48805, which is incorporated herein by reference.

The partial oxidation catalyst may comprise a rhodium gauze or rhodium felt as disclosed in PCT International Publication No. WO 01/80992A2, which is incorporated herein by reference.

The partial oxidation catalyst may comprise a rhodium-spinel catalyst as disclosed in PCT International Publication No. WO 02/066403A1, which is incorporated herein by reference.

The partial oxidation catalyst may comprise a Group VIII metal (e.g., Ru, Rh, Pd, Os, Ir, Pt) supported on a refractory oxide having at least two cations as disclosed in EP 0640561A1, which is incorporated herein by reference.

The partial oxidation catalyst may comprise rhodium and/or ruthenium having a layered hydrotalcite type structure as disclosed in EP 0725038A1, which is incorporated herein by reference.

The partial oxidation catalyst may comprise a nickel-based catalyst or ruthenium based catalyst as disclosed in EP 0741107A2, which is incorporated herein by reference.

The partial oxidation catalyst may comprise a composition represented by the formula $$M^1_a M^2_b M^3_c Al_d O_x \qquad (I)$$

wherein in formula (I): $M^1$ is Rh, Ni, Pd, Pt, Ru, Co or a mixture of two or more thereof; $M^2$ is Ce, Pr, Tb or a mixture of two or more thereof; $M^3$ is La, Ba, Zr, Mg, Ca or a mixture of two or more thereof; a is a number in the range of about 0.0001 to about 1, and in one embodiment 0.01 to about 1; b is a number in the range of zero to about 0.9999, and in one embodiment zero to about 0.2; c is a number in the range of about 0.0001 to about 0.9999, and in one embodiment about 0.01 to about 0.2; d is a number in the range of about 0.0001 to about 0.9999, and in one embodiment about 0.1 to about 0.9; and x is the number of oxygens needed to fulfill the valency requirements of the elements present; the catalyst being coated on a substrate or supported on a foam, felt, wad or fin. In one embodiment $M^1$ is Rh or Ni, and in one embodiment it is Rh. In one embodiment $M^3$ is La or Mg, and in one embodiment it is La. In one embodiment the catalyst may be represented by the formula $Rh/LaAl_{11}O_{18}$ or $Rh/LaAlO_3$.

In one embodiment, the process for making the catalyst represented by formula (I) comprises the steps of: (A) applying a layer of $Al_2O_3$ over the native oxide layer to form a treated support structure; (B) calcining the treated support structure formed in step (A); (C) applying a promoter or stabilizer to the surface of the calcined support structure formed in step (B), the promoter or stabilizer comprising La, Ba, Zr, Mg, Ca, or an oxide or nitrate thereof, or a mixture of two or more thereof; (D) calcining the treated support structure formed in step (C); (E) applying a catalytic metal, or oxide or nitrate thereof, to the surface of the calcined support structure formed in step (D), the catalytic metal comprising Rh, Ni, Pd, Pt, Ru, Co, or a mixture of two or more thereof; and (F) calcining the treated support structure formed in step (F) to form the supported catalyst. In one embodiment, the catalyst formed in step (F) may be reduced in hydrogen.

The support structure may be made of a material comprising: steel; aluminum; titanium; iron; nickel; platinum; rhodium; copper; chromium; brass; an alloy of any of the foregoing metals; a polymer; ceramics; glass; a composite comprising polymer and fiberglass; quartz; silicon; or a combination of two or more thereof. In one embodiment the support structure may be made of an alloy comprising Fe, Cr, Al and Y, and the native oxide layer may comprise $Al_2O_3$. In one embodiment, the support structure may be made of an alloy comprising Ni, Cr and Fe, and the native oxide layer may comprise $Cr_2O_3$. In one embodiment, the promoter or stabilizer may be La or Mg, and in one embodiment it is La. In one embodiment, the catalytic metal is Rh or Ni, and in one embodiment it is Rh.

The support structure may be heated prior to step (A) to a temperature in the range of about 300° C. to about 1400° C., and in one embodiment about 700 to about 1200° C., for about 0.1 to about 1000 hours, and in one embodiment about 1 to about 10 hours. When the support structure is made of metal, this heat treating step advantageously provides a layer of native oxide on the surface of the support structure.

During step (A) a slurry comprising $Al_2O_3$ or a colloidal dispersion (i.e., a sol) comprising $Al_2O_3$ may be applied over the native oxide layer. The slurry may comprise about 1 to about 50% by weight $Al_2O_3$, up to about 20% by weight $ZrO_2$, up to about 25% by weight $La(NO_3).6H_2O$, with the remainder being water. The slurry coating may have a thickness of about 10 to about 100 microns. The colloidal dispersion may contain about 1% to about 30% by weight $Al_2O_3$ with the remainder being water. The colloidal dispersion coating may have a thickness of about 1 to about 50 microns.

During step (B) the treated support structure may be calcined in air at a temperature in the range of about 150° C. to about 1200° C., and in one embodiment about 300 to about 700° C., for about 0.1 to about 1000 hours, and in one embodiment about 1 to about 10 hours.

During step (C) a solution comprising $La(NO_3)_3$ may be applied to the surface of the calcined support structure.

During step (D) the treated support structure may be calcined in air at a temperature in the range of about 150° C. to about 1200° C., and in one embodiment about 500 to about 1100° C., for about 0.1 to about 1000 hours, and in one embodiment about 1 to about 10 hours.

During step (E) a composition comprising $Rh(NO_3)_3$ may be applied to the surface of the calcined support structure.

During step (F) the treated support structure may be calcined in air at a temperature in the range of about 150° C. to about 1200° C., and in one embodiment about 400° C. to about 1100° C., for about 0.1 to about 1000 hours, and in one embodiment about 1 to about 10 hours.

The combustion catalyst may comprise any combustion catalyst. These include, for example, noble metals such as Pt, Rh, Pd, Co, Cu, Mn, Fe, Ni; oxides of any of these metals; perovskites and aluminates. In one embodiment, the combustion catalyst is accompanied by an activity-enhancing promoter such as Ce, Tb or Pr, their oxides, and combinations thereof. In one embodiment, a promoter element is present in at least about 1:1 molar ratio as compared to the active catalyst element or elements, and in one embodiment a promoter element is present in the range of about 0.5:1 to about 10:1 molar ratio as compared to an active catalyst element (moles promoter(s): moles active catalyst element(s)). These catalysts may be in any of the forms or supported on any of the support structures discussed above.

The contact time of the reactants and/or products with the catalyst within the process microchannels may range up to about 500 milliseconds (ms), and in one embodiment from about 0.1 ms to about 500 ms, and in one embodiment about 0.1 ms to about 400 ms, and in one embodiment about 0.1 ms to about 300 ms, and in one embodiment about 0.1 ms to about 200 ms, and in one embodiment about 0.1 ms to about 100 ms, and in one embodiment from about 1 ms to about 75 ms, and in one embodiment about 1 ms to about 50 ms, and in one embodiment about 1 ms to about 25 ms, and in one embodiment about 1 ms to about 10 ms, and in one embodiment about 1 ms to about 5 ms.

The space velocity (or gas hourly space velocity) for the flow of the reactant composition and product through the process microchannels may be at least about 100 $hr^{-1}$ (normal liters of hydrocarbon/hour/liter of reaction chamber) or at least about 100 ml feed/(g catalyst) (hr). The space velocity may range from about 100 to about 2,000,000 $hr^{-1}$ based on the volume of the process microchannels, or from about 100 to about 2,000,000 ml feed/(g catalyst) (hr). In one embodiment, the space velocity may range from about 500 to about 1,000,000 $hr^{-1}$, or about 500 to about 1,000,000 ml feed/(g catalyst) (hr), and in one embodiment from about 1000 to about 1,000,000 $hr^{-1}$, or from about 1000 to about 1,000,000 ml feed/(g catalyst) (hr).

The temperature of the reactant composition entering the process microchannels may range from about 200° C. to about 1000° C., and in one embodiment about 150° C. to about 700° C., and in one embodiment about 150° C. to about 600° C., and in one embodiment about 200° C. to about 600° C. In one embodiment the temperature may be in the range of about 150° C. to about 500° C., and in one embodiment about 150° C. to about 400° C., and in one embodiment about 200° C. to about 300° C. In one embodiment, the temperature may be in the range of about 335° C. to about 1000° C.

The temperature of the reactant composition and product within the process microchannel may range up to about 1150° C., and in one embodiment up to about 1100° C., and in one embodiment up to about 1050° C., and in one embodiment up to about 1000° C., and in one embodiment up to about 950° C., and in one embodiment up to about 900° C., and in one embodiment up to about 850° C., and in one embodiment up to about 800° C., and in one embodiment up to about 750° C., and in one embodiment up to about 700° C.

The reactant composition entering the process microchannels may be at a pressure of at least about 0.1 atmosphere, and in one embodiment at least about 0.5 atmosphere. In one embodiment the pressure may range from about 0.1 to about 100 atmospheres, and in one embodiment from about 0.5 to about 50 atmospheres, and in one embodiment about 1 to about 40 atmospheres, and in one embodiment from about 1 to about 35 atmospheres.

The pressure drop of the reactants and/or products as they flow through the process microchannels may range up to about 2 atmospheres per meter of length of the process microchannel (atm/m), and in one embodiment up to about 1 atm/m, and in one embodiment up to about 0.5 atm/m, and in one embodiment up to about 0.2 atm/m.

The flow of the reactants and/or products through the process microchannels may be laminar or in transition, and in one embodiment it is laminar. The Reynolds Number for the flow of reactants and/or products through the process microchannels may be up to about 4000, and in one embodiment up to about 2300, and in one embodiment in the range of about 10 to about 2000, and in one embodiment about 100 to about 1500.

The heat exchange fluid entering the heat exchange channels may have a temperature of about −70° C. to about 650° C., and in one embodiment about 0° C. to about 500° C., and in one embodiment about 100° C. to about 300° C. The heat exchange fluid exiting the heat exchange channels may have a temperature in the range of about −60° C. to about 630° C., and in one embodiment about 10° C. to about 490° C. The residence time of the heat exchange fluid in the heat exchange channels may range from about 1 to about 1000 ms, and in one embodiment about 1 to about 500 ms, and in one embodiment from 1 to about 100 ms. The pressure drop for the heat exchange fluid as it flows through the heat exchange channels may range from about 0.05 to about 50 psi/ft, and in one embodiment from about 1 to about 25 psi/ft. The flow of the heat exchange fluid through the heat exchange channels may be laminar or in transition, and in one embodiment it is laminar. The Reynolds Number for the flow of heat exchange fluid flowing through the heat exchange channels may be up to about 4000, and in one embodiment up to about 2300, and in one embodiment in the range of about 10 to about 2000, and in one embodiment about 10 to about 1500.

The product exiting the microchannel reactor may be at a temperature in the range of about 100° C. to about 1000° C., and in one embodiment about 200° C. to about 800° C., and in one embodiment about 300° C. to about 600° C. The product may be cooled to a temperature in the range of about 50° C. to about 300° C., and in one embodiment about 50° C. to about 200° C., and in one embodiment about 50° C. to 150° C., and in one embodiment about 50° C. to about 100° C., in about 5 to about 100 ms, and in one embodiment about 5 to about 75 ms, and in one embodiment about 5 to about 50 ms, and in one embodiment about 10 to about 50 ms.

Advantages of the inventive process include: maximization of contact between the hydrocarbon reactant, oxygen or source of oxygen, and the catalyst; and minimization of undesired reactions.

Advantages of the inventive process include the possibility of process intensification. Conventional processes of the prior art often operate under conditions of reactant dilution to prevent runaway reactions, while the inventive process may be operated, if desired, under more intensive conditions leading to greater throughput. By combining catalytic microchannel processing with heat exchange it is possible to operate at hydrocarbon feed/oxygen ratios that would conventionally lead to high temperatures and loss of selectivity, but by removing heat rapidly through heat exchange, the temperature in the process microchannels may be maintained relatively low, for example, below about 700° C., and in one embodiment below about 600° C., and in one embodiment below about 500° C., thus maximizing selectivity to desired products.

Advantages of the inventive process include the enhancement of reaction selectivity due to the dimensions of the microchannel reactor. In reactors of conventional dimension, reactions propagated homogeneously in the in the gaseous phase make a significant contribution to the overall make-up of the product. These reactions tend to be indiscriminate and often result in the production of undesirable by-products such as CO and $CO_2$ or hydrocarbon pyrolysis products. For example, if the reactant mixture contains propane, full and partial oxidation can take place as well as pyrolysis leading to the production of ethane and methane.

The level of conversion of the hydrocarbon reactant may be about 50% or higher, and in one embodiment about 60% or higher, and in one embodiment about 70% or higher, and in one embodiment about 80% or higher.

The level of selectivity of the desired product may be about 30% or higher, and in one embodiment about 50% or higher, and in one embodiment about 60% or higher, and in one embodiment about 70% or higher, and in one embodiment about 80% or higher, and in one embodiment about 85% or higher, and in one embodiment about 90% or higher, and in one embodiment about 95% or higher. In one embodiment, the level of selectivity to the desired product may be in the range of about 50% to about 95%, and in one embodiment about 75% to about 95%.

The yield of the desired product may be about 9% or higher per cycle, and in one embodiment about 20% or higher, and in one embodiment about 40% or higher, and in one embodiment about 50% or higher per cycle, and in one embodiment about 70% or higher, and in one embodiment 80% or higher, and in one embodiment about 90% or higher per cycle. The term "cycle" is used herein to refer to a single pass of the reactants through the process microchannels.

In one embodiment, the level of conversion of the hydrocarbon reactant is at least about 30%, the level of selectivity of the desired product is at least about 30%, and the yield of the desired product is at least about 9% per cycle.

In one embodiment, the process is conducted in a reactor containing a plurality of heat exchange channels operating in parallel, the total pressure drop for the heat exchange fluid flowing through the heat exchange channels is up to about 10 atmospheres, and in one embodiment up to about 5 atmospheres, and in one embodiment up to about 2 atmospheres.

EXAMPLE 1

$La_2O_3$ stabilized $Al_2O_3$ is synthesized by using a sol-gel technique as follows. 24.7 g of aluminum butoxide are dissolved into 74.5 g of 2-butanol in a beaker with constant stirring. In another beaker, 4.0 g of $La(NO_3)_3 \cdot 6H_2O$ are dissolved into 59.7 g of ethanol with constant stirring. The two solutions are mixed and stirred for 15 min. Subsequently 4.4 g of deionized $H_2O$ are added slowly into the mixture. The obtained solution is heated to 80–100° C. and kept it at this temperature for 2 hours. The alcohols are vaporized during this time. The resulting solid is dried at 120° C. overnight and calcined at 1000° C. for 24 hours in air at a heating and cooling rate of 4° C./min. The resulting material has 22 wt. % $La_2O_3$ and 78 wt. % $Al_2O_3$. Its BET surface area and pore volume are 64 $m^2/g$ and 0.35 $cm^3/g$, respectively. The solid is crushed and 88–150 microns particles are chosen as catalyst support.

Rh/$La_2O_3$—$Al_2O_3$ catalyst is prepared by incipient wetness impregnation as follows. 0.96 g of 10 wt. % $Rh(NO_3)_3$ solution are dropped onto 0.8 g of the $La_2O_3$—$Al_2O_3$ particles. After drying at 120° C. for 1 hour, the sample is calcined at 500° C. for 1 hour in air at a heating and cooling rate of 3.5° C./min. This impregnation process is repeated once. The catalyst is calcined at 800° C. for 1 hour. The Rh loading is 8.0 wt. %.

30 mg of catalyst are loaded in a tube reactor for testing partial oxidation of methane activity. The catalyst is reduced with $H_2$ at 450° C. for 30 min before use. The feed gas composition contains 29.6% of $CH_4$ and 70.4% of air ($CH_4/O_2=2/1$), with 3.4 standard liters per minute (SLPM). The gas hourly space velocity (GHSV) is $5.8 \times 10^6 h^{-1}$. $CH_4$ conversion is calculated by the difference in methane flow rates before the reaction and after the reaction. CO selectivity is obtained by $[CO]/([CO]+[CO_2])$ and $H_2$ selectivity is calculated by $[H_2]/([H_2]+[H_2O])$. At a tube skin temperature of 700° C., 88% of $CH_4$ conversion, 97% of CO selectivity and 91% of $H_2$ selectivity are obtained. $O_2$ conversion is 100%.

EXAMPLE 2

$La_2O_3$ stabilized $Al_2O_3$ was synthesized by a sol-gel technique as follows. 24.7 g of aluminum butoxide are dissolved into 74.5 g of 2-butanol in a beaker with stirring. In another beaker, 4.0 g of $La(NO_3)_3 \cdot 6H_2O$ are dissolved into 59.7 g of ethanol with stirring. The two solutions are mixed and stirred for 15 min. Subsequently 4.4 g of deionized $H_2O$ are added slowly into the mixture. The obtained solution is heated to 80–100° C. and maintained at this temperature for 2 hours. The alcohols are vaporized during this time. The resulting solid is dried at 120° C. overnight and calcined at 1000° C. for 24 hours in air at a heating and cooling rate of 4° C./min. The resulting material contains 22 wt. % $La_2O_3$ and 78 wt. % $Al_2O_3$. Its BET surface area and pore volume are 64 m²/g and 0.35 cm³/g, respectively. The solid is crushed and 88–150 microns particles are chosen as catalyst support.

Rh/La$_2$O$_3$—Al$_2$O$_3$ catalyst is prepared by incipient wetness impregnation as follows. 0.96 g of 10 wt. % Rh(NO$_3$)$_3$ solution are dropped onto 0.8 g of the La$_2$O$_3$—Al$_2$O$_3$ particles. After drying at 120° C. for 1 hour, the sample is calcined at 500° C. for 1 hour in air at a heating and cooling rate of 3.5° C./min. This impregnation process is repeated once. The catalyst is calcined at 1000° C. for 1 hour. The Rh loading is 8.0 wt. %.

30 mg of catalyst are loaded in a tube reactor for testing partial oxidation of methane activity. The catalyst is reduced with H$_2$ at 450° C. for 30 min before use. The feed gas compositions are 29.6% of CH$_4$ and 70.4% of air (CH$_4$/O$_2$=2/1), with 3.4 SLPM. GHSV is 5.8×10⁶h⁻¹. The tube skin temperature is 700° C. 90% of CH$_4$ conversion, 97% of CO selectivity and 87% of H$_2$ selectivity are obtained. O$_2$ conversion is 100%. The process is conducted for 260 hours. The results are disclosed in FIG. 8.

Figure 8:
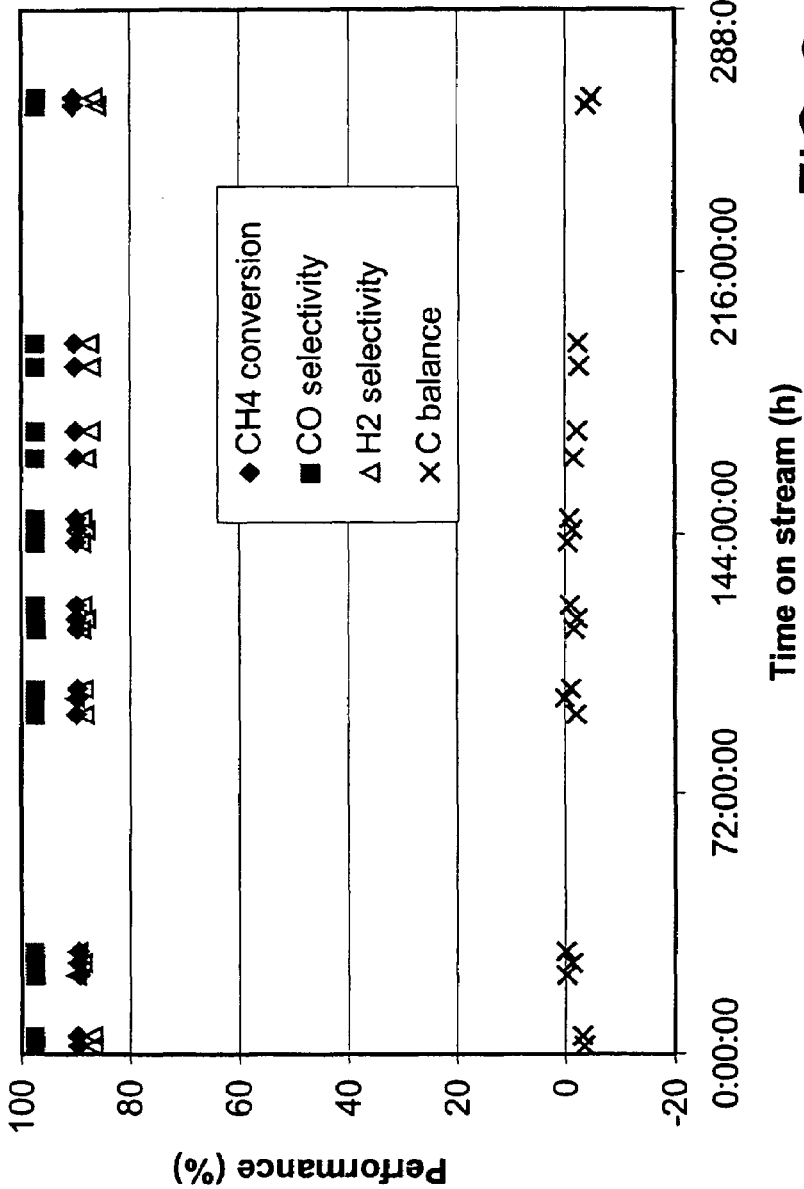
FIG. 8 is a plot of process performance versus time for the tests disclosed in Example 2.

These tests results indicate that this catalyst is very stable. As shown in FIG. 8, CH$_4$ conversion, CO selectivity and H$_2$ selectivity are substantially unchanged during 260 hours time-on-stream. These results demonstrate that the Rh/La$_2$O$_3$—Al$_2$O$_3$ catalyst is highly active for the partial oxidation of methane to CO and H$_2$ at an extremely high space velocity.

EXAMPLE 3

FIG. 7 shows the geometry of a fin that is useful for conducting a partial oxidation reaction process in a process microchannel. The trapezoidal shape of the fins provides mechanical rigidity at the base of fins. All the fins are supported on rectangular base to enhance heat transfer characteristics of the fin. The fin is fabricated from FeCrAlY using the Wire EDM method. The following table summarizes dimensions of the fin:

|  | Dimension (in) |
|---|---|
| Fin thickness | |
| At base | 0.005 |
| At top | 0.002 |
| Fin spacing | |
| At base | 0.012 |
| At top | 0.017 |
| Fin height | 0.029 |
| Rectangular base height | 0.020 |
| Overall width | 0.180 |
| Overall Height | 0.049 |
| Overall length | 1.500 |

An Al$_2$O$_3$ slurry is prepared by mixing 7.2 g of gamma Al$_2$O$_3$ powder, 12 g of deionized H$_2$O and 42 g Al$_2$O$_3$ beads with 3 mm diameter. The pH value is adjusted to 3.5–4 using nitric acid. The Al$_2$O$_3$ is acidic gamma Al$_2$O$_3$ which is ground to powder smaller than 150 micrometers. The mixture is ball-milled for 8 hours. 0.8 g of 25 wt. % Al$_2$O$_3$ sol (Sasol 14N4-25) is added to 4.2 g of the slurry with stirring.

The FeCrAlY fin is cleaned in iso-propanol for 20 min with sonication. After drying at 100° C. for 1 h and cooling to room temperature, the fin is cleaned in 20 wt. % HNO$_3$ solution for 20 min with sonication. The fin is then rinsed with deionized water until the pH value is 7. After drying at 120° C. for 1 hour, the fin is heated to 1000° C. in air at a heating rate of 3.5° C./min and calcined at 1000° C. for 8 hours in air. A dense Al$_2$O$_3$ layer is generated after the calcination. The Al$_2$O$_3$ layer functions as a protection scale and also improves the adhesion between the coating and the fin. The Al$_2$O$_3$ slurry is washcoated onto the fin by dipping. The excess slurry is removed by jetting air over the coated surface. The fin is dried at 120° C. for 1 hour and then calcined at 450° C. for 4 hours at a heating and cooling rate of 3.5° C./min. A 7.5 wt. % La(NO$_3$)$_3$ solution is impregnated onto the fin by dipping. The fin is dried at 120° C. for 1 hour and then calcined at 1000° C. for 4 hours in air at a heating and cooling rate of 3.5° C./min. The La$_2$O$_3$ on the surface stabilizes the Al$_2$O$_3$. The slurry loading is 25.4 mg per fin. A 10 wt. % Rh(NO$_3$)$_3$ solution is dropped onto the fin and the excess solution is blown out by compressed air. The resulting fin supported catalyst is dried at 120° C. for 1 hour and then calcined at 1000° C. for 1 h in air. The Rh loading is 4.8 mg per fin.

The fin supported catalyst is tested for partial oxidation of methane to syngas at 1 atmosphere in a pellet. The pellet is a cylindrical metal rod having a diameter of 0.5 inch and a length of 2 inches. The pellet has a rectangular microchannel cut-away in its center. The cut-away extends through the rod along its interior axis. The cut-away has a height of 0.05 inch and a width of 0.18 inch. The fin supported catalyst is placed in the cut-away for testing. Gas tight connections are made on each side of the cut-away. The reactants flow through tubing to the cut-away, and through the cut-away in contact with the fin supported catalyst. The pellet is placed in a furnace. The temperature of the furnace is increased to keep the pellet outside skin temperature at mid-length at 850° C. The temperature of the feed stream at the inlet of the furnace is at room temperature and is preheated before entering the pellet. The length of the tubing from the entrance of the furnace to the pellet is 10 feet. The outlet pressure of the product stream is atmospheric pressure. The pressure drop in the pellet is measured using a Capsuhelic differential pressure gauge. The composition of the product is analyzed with a two-column Gas Chromatograph. The performance of the fin supported catalyst is measured in terms of CH$_4$ conversion, H$_2$ selectivity and CO selectivity.

CH$_4$ Conversion (%)=(V$_{CH4}$, in −V$_{CH4}$, out)/(V$_{CH4}$, in)×100

H$_2$ Selectivity (%)=(V$_{H2}$, out, actual)/(V$_{H2}$, out, theoretical)×100

CO Selectivity (%)=(V$_{CO}$, out)/(V$_{CO}$, out+V$_{CO2}$, out)×100

The catalyst is reduced with H$_2$ at 400° C. for 30 min before use. The feed gas compositions are 29.6% of CH$_4$ and 70.4% of air (CH$_4$/O$_2$=2/1), with 2030 ml/min of total flow rate (standard conditions). The contact time is 3.3 ms. The contact time is defined as the ratio of flow volume in the pellet without the fin to the volumetric flow rate. The following table summarizes the fin supported catalyst performance after 157 hours of operation.

| Parameter | Value |
|---|---|
| Coating Type | Powder slurry wash-coat |
| Fuel composition | 29.6% CH$_4$, 70.4% air |
| Fuel contact time | 3.3 ms |
| CH$_4$ Conversion (at 850° C.) | 85% |
| H$_2$ Selectivity (at 850° C.) | 92% |

| Parameter | Value |
| --- | --- |
| CO Selectivity (at 850° C.) | 95% |
| Pressure drop | 5.6 psi |

EXAMPLE 4

An alternate fin for use in a partial oxidation reaction process provides the advantage of reduced pressure drop. The flow area is increased by reducing number of fins. There are five fins projecting up from the fin support. The fins have a trapezoidal cross section as indicated in FIG. 7. The thickness of the fin along with trapezoidal shape of the fins provides mechanical rigidity at the base of the fins. The fins are supported on rectangular support or base to enhance heat transfer characteristics of the fin. The fin is made from FeCrAlY. The fin is fabricated by the wire EDM method. The following table summarizes dimensions of the fin:

| | Dimension (in) |
| --- | --- |
| Fin Thickness | |
| At base | 0.020" |
| At top | 0.010" |
| Fin spacing | |
| At base | 0.012" |
| At top | 0.022" |
| Fin height | 0.033" |
| Rectangular base height | 0.020" |
| Overall width | 0.180" |
| Overall height | 0.053" |
| Overall length | 1.500" |

An $Al_2O_3$ slurry is prepared by mixing 7.2 g of gamma $Al_2O_3$ powder, 12 g of deionized $H_2O$ and 42 g $Al_2O_3$ beads with 3 mm diameter. The pH value is adjusted to 3.5–4 using nitric acid. The $Al_2O_3$ is acidic gamma $Al_2O_3$ and is ground to powder smaller than 150 micrometers. The mixture is then ball-milled for 8 hours. 0.8 g of 25 wt. % $Al_2O_3$ sol (Sasol 14N4-25) is added to 4.2 g of the slurry with stirring.

The FeCrAlY fin is cleaned in iso-propanol for 20 min with sonication. After drying at 100° C. for 1 hour and cooling to room temperature, the fin is cleaned in 20 wt. % $HNO_3$ solution for 20 min with sonication. The fin is rinsed with deionized water until the pH value is 7. After drying at 120° C. for 1 hour, the fin is heated to 1000° C. in air at a heating rate of 3.5° C./min and calcined at 1000° C. for 8 hours in air. The $Al_2O_3$ slurry is washcoated onto the fin by dipping. The excess slurry is removed by jetting air over the coated surface. The fin is dried at 120° C. for 1 hour and then calcined at 450° C. for 4 hours at a heating and cooling rate of 3.5° C./min. A 7.5 wt. % $La(NO_3)_3$ solution is impregnated onto the slurry-coated fin by dipping. The fin is dried at 120° C. for 1 hour and calcined at 1000° C. for 4 hours in air at a heating and cooling rate of 3.5° C./min. The slurry loading is 6.0 mg per fin. A 10 wt. % $Rh(NO_3)_3$ solution is dropped onto the fin and the excess solution is blown out by compressed air. The fin is dried at 120° C. for 1 hour and then calcined at 1000° C. for 1 hour in air. The Rh loading is 1.0 mg per fin.

The resulting fin supported catalyst is tested for partial oxidation of methane to syngas at 1 atmosphere in the pellet described in Example 3. The pellet is placed in a furnace. The temperature of the furnace is adjusted to keep the pellet skin temperature at mid-length at 805° C. The temperature of the feed stream at the inlet of furnace is at room temperature. The feed stream is preheated before entering the pellet. The length of tubing from the entrance of furnace to the pellet is 10 feet. The outlet pressure of the product stream is atmospheric pressure. The pressure drop in the pellet is the difference between the inlet and the outlet pressures. The composition of product is analyzed with a two-column Gas Chromatograph. The performance of the fin is measured in terms of $CH_4$ conversion, $H_2$ selectivity and CO selectivity. The following table summarizes catalyst performance for the fin after 115 hours of operation.

| Parameter | Value |
| --- | --- |
| Coating Type | Powder slurry wash-coat |
| Fuel composition | 29.6% $CH_4$, 70.4% air |
| Fuel contact time | 3.3 ms |
| $CH_4$ Conversion (at 850° C.) | 78% |
| $H_2$ Selectivity (at 850° C.) | 93% |
| CO Selectivity (at 850° C.) | 93% |
| Pressure drop | 2.8 psi |

EXAMPLE 5

An FeCrAlY fin is fabricated with saw-cut method and tested for catalyst performance. The following table summarizes dimensions of the fin:

| | Dimension (in) |
| --- | --- |
| Fin Thickness | |
| At base | 0.010" |
| At top | 0.005" |
| Fin spacing | |
| At base | 0.017" |
| At top | 0.022" |
| Fin height | 0.033" |
| Rectangular base height | 0.020" |
| Overall width | 0.180" |
| Overall height | 0.053" |
| Overall length | 1.500" |

An $Al_2O_3$ slurry is prepared by mixing 7.2 g of gamma $Al_2O_3$ powder, 12 g of deionized $H_2O$ and 42 g $Al_2O_3$ beads with 3 mm diameter. The pH value was adjusted to 3.5–4 using nitric acid. The $Al_2O_3$ is acidic gamma $Al_2O_3$, is ground to powder smaller than 150 micrometers. The mixture is then ball-milled for 8 hours. 0.8 g of 25 wt. % $Al_2O_3$ sol (Sasol 14N4-25) is added to 4.2 g of the slurry with stirring.

The FeCrAlY fin is cleaned in iso-propanol for 20 min with sonication. After drying at 100° C. for 1 hour and cooling to room temperature, the fin is cleaned in 20 wt. % $HNO_3$ solution for 20 min with sonication. The fin is then rinsed with deionized water until pH value reaches 7. After drying at 120° C. for 1 hour, the fin is heated to 1000° C. in air at a heating rate of 3.5° C./min and calcined at 1000° C. for 8 hours in air. The $Al_2O_3$ slurry is washcoated onto the fin by dipping. The excess slurry is removed by jetting air over the coated surface. The fin is dried at 120° C. for 1 hour and then calcined at 450° C. for 4 hours at a heating and cooling rate of 3.5° C./min. 7.5 wt. % La(NO$_3$)$_3$ solution is impregnated onto the slurry-coated fin by dipping. The fin is dried at 120° C. for 1 hour and calcined at 1000° C. for 4 hours in air at a heating and cooling rate of 3.5° C./min. The slurry loading is 18.7 mg per fin. 10 wt. % Rh(NO$_3$)$_3$ solution is dropped onto the fin and the excess solution is blown out by compressed air. The fin is dried at 120° C. for 1 hour and calcined at 1000° C. for 4 hours in air. The Rh loading is 3.2 mg per fin.

The resulting fin supported catalyst is tested for partial oxidation of methane at 1 atmosphere in the pellet described in Example 3. The pellet is placed in a furnace. The catalyst is reduced with H$_2$ at 400° C. for 30 min before use. The feed gas compositions are 29.6% of CH$_4$ and 70.4% of air (CH$_4$/O$_2$=2/1), with 2372 ml/min of total flow rate (standard conditions). The contact time is 3.3. The temperature of the furnace is adjusted to keep the pellet skin temperature at mid-length at 850° C. The temperature of the feed stream at the inlet of furnace is at room temperature. The feed stream is preheated before entering pellet. The length of tubing from the entrance of furnace to the pellet is 10 feet. The outlet pressure of the product stream is atmospheric pressure. The pressure drop in the pellet is measured by a capsuhelic differential pressure gauge. The composition of product is analyzed with a two-column Gas Chromatograph. The performance of the fin is measured in terms of CH$_4$ conversion, H$_2$ selectivity and CO selectivity. The following table summarizes the fin supported catalyst performance after 400 hours of operation.

| Parameter | Value |
| --- | --- |
| Coating Type | Powder slurry wash-coat |
| Fuel composition | 29.6% CH$_4$, 70.4% air |
| Fuel contact time | 3.3 ms |
| CH$_4$ Conversion (at 850° C.) | 75% |
| H$_2$ Selectivity (at 850° C.) | 72% |
| CO Selectivity (at 850° C.) | 91% |
| Pressure drop | 2.1 psi |

EXAMPLE 6

A fin having the same dimensions as the fin in Example 5 is cleaned in iso-propanol for 20 min with sonication. After drying at 100° C. for 1 hour and cooling to room temperature, the fin is cleaned in 20 wt. % HNO$_3$ solution for 20 min with sonication. The fin is rinsed with deionized water until the pH value reaches 7. After drying at 120° C. for 1 hour, the fin is heated to 1000° C. in air at a heating rate of 3.5° C./min and calcined at 1000° C. for 8 hours in air. A dense Al$_2$O$_3$ layer is generated after calcination. The Al$_2$O$_3$ layer-functions as a protection scale and also improves the adhesion between the coating and the fin. Al$_2$O$_3$ sol (25 wt. %, Sasol 14N4-25) is coated onto the fin by dipping. The excess sol is removed by jetting air over the coated surface. The fin is dried at 120° C. for 1 hour and calcined at 450° C. for 4 hours at a heating and cooling rate of 3.5° C./min. The sol coating process is repeated 3 to 4 times until 17 mg of Al$_2$O$_3$ loading per fin is achieved. 7.5 wt. % La(NO$_3$)$_3$ solution is impregnated onto the fin by dipping. The fin is dried at 120° C. for 1 hour and calcined at 1000° C. for 4 hours in air at a heating and cooling rate of 3.5° C./min. 10 wt. % Rh(NO$_3$)$_3$ solution is dropped onto the fin and the excess solution is blown out by compressed air. The fin is dried at 120° C. for 1 hour and calcined at 500° C. for 1 hour in air.

The Rh(NO$_3$)$_3$ solution coating is repeated once and the fin is calcined at 1000° C. for 4 hours. The Rh loading is 5.2 mg per fin.

The resulting fin supported catalyst is tested for partial oxidation of methane to syngas at 1 atmosphere using the pellet described in Example 3. The pellet is placed in a furnace. The catalyst is reduced with H$_2$ at 450° C. for 30 min before use. The feed gas compositions were 29.6% of CH$_4$ and 70.4% of air (CH$_4$/O$_2$=2/1), with 2361 ml/min of total flow rate (standard conditions). The contact time is 3.3 ms. The temperature of the furnace is adjusted to keep the pellet skin temperature at mid-length at 800° C. The temperature of the feed stream at the inlet of the furnace is at room temperature. The feed stream is preheated before entering the pellet. The length of tubing from the entrance of furnace to the pellet is ten feet. The outlet pressure of the product stream is atmospheric pressure. The pressure drop in the pellet is measured by capsuhelic differential pressure gauge. The composition of product is analyzed with two-column Gas Chromatograph. The performance of the fin is measured in terms of CH$_4$ conversion, H$_2$ selectivity and CO selectivity. The performance of the fin supported catalyst after 600 hours of steady-state operation is indicated below.

| Parameter | Value |
| --- | --- |
| Coating Type | Sol wash-coat |
| Fuel composition | 29.6% CH$_4$, 70.4% air |
| Fuel contact time | 3.3 ms |
| CH$_4$ Conversion (at 800° C.) | 71% |
| H$_2$ Selectivity (at 800° C.) | 70% |
| CO Selectivity (at 800° C.) | 87% |
| Pressure drop | 1.4 psi |

The foregoing fin supported catalyst is tested with an n-butane and CH$_4$ fuel mixture. The feed gas contains 7.2% CH$_4$, 7.2% n-butane and 85.6% air with a total flow rate of 2091 ml/min. A four column gas chromatograph is used to analyze the outlet gas composition. The temperature of the furnace is adjusted to keep pellet skin temperature at mid-length at 800° C. The performance of the fin supported catalyst after 300 hours of operation is summarized below.

| Parameter | Value |
| --- | --- |
| CoatingType | Powder slurry wash-coat |
| Fuel composition | 7.5% CH$_4$, 7.5% n-butane, 85% air |
| Fuel contact time | 3.3 ms |
| CH$_4$ Conversion (at 800° C.) | 60% |
| n-butane conversion (at 800° C.) | 76% |
| H$_2$ Selectivity (at 800° C.) | 77% |
| CO Selectivity (at 800° C.) | 82% |
| Pressure drop | 1.0 psi |

EXAMPLE 7

A fin having the same dimensions as the fin in Example 3 is cleaned in iso-propanol for 20 min with sonication. After drying at 100° C. for 1 hour and cooling to room temperature, the fin is cleaned in 20 wt. % HNO$_3$ solution for 20 min with sonication. The fin is rinsed with deionized water until the pH value reaches 7. After drying at 120° C. for 1 hour, the fin is heated to 1000° C. in air at a heating rate of 3.5° C./min and calcined at 1000° C. for 8 hours in air. A dense $Al_2O_3$ layer is generated after calcination. The $Al_2O_3$ layer functions as a protection scale and also improves the adhesion between the coating and the fin. $Al_2O_3$ sol (25 wt. %, Sasol 14N4-25) is coated onto the fin by dipping. The excess sol is removed by jetting air over the coated surface. The fin is dried at 120° C. for 1 hour and calcined at 450° C. for 4 hours at a heating and cooling rate of 3.5° C./min. The sol coating process is repeated 4 to 5 times until 22 mg of $Al_2O_3$ loading per fin is achieved. 7.5 wt. % $La(NO_3)_3$ solution is impregnated onto the fin by dipping. The fin is dried at 120° C. for 1 hour and calcined at 1000° C. for 4 hours in air at a heating and cooling rate of 3.5° C./min. 10 wt. % $Rh(NO_3)_3$ solution is dropped onto the fin and the excess solution is blown out by compressed air. The fin is dried at 120° C. for 1 hour and calcined at 1000° C. for 1 hour in air. The Rh loading is 1.5 mg per fin.

Figure 9:
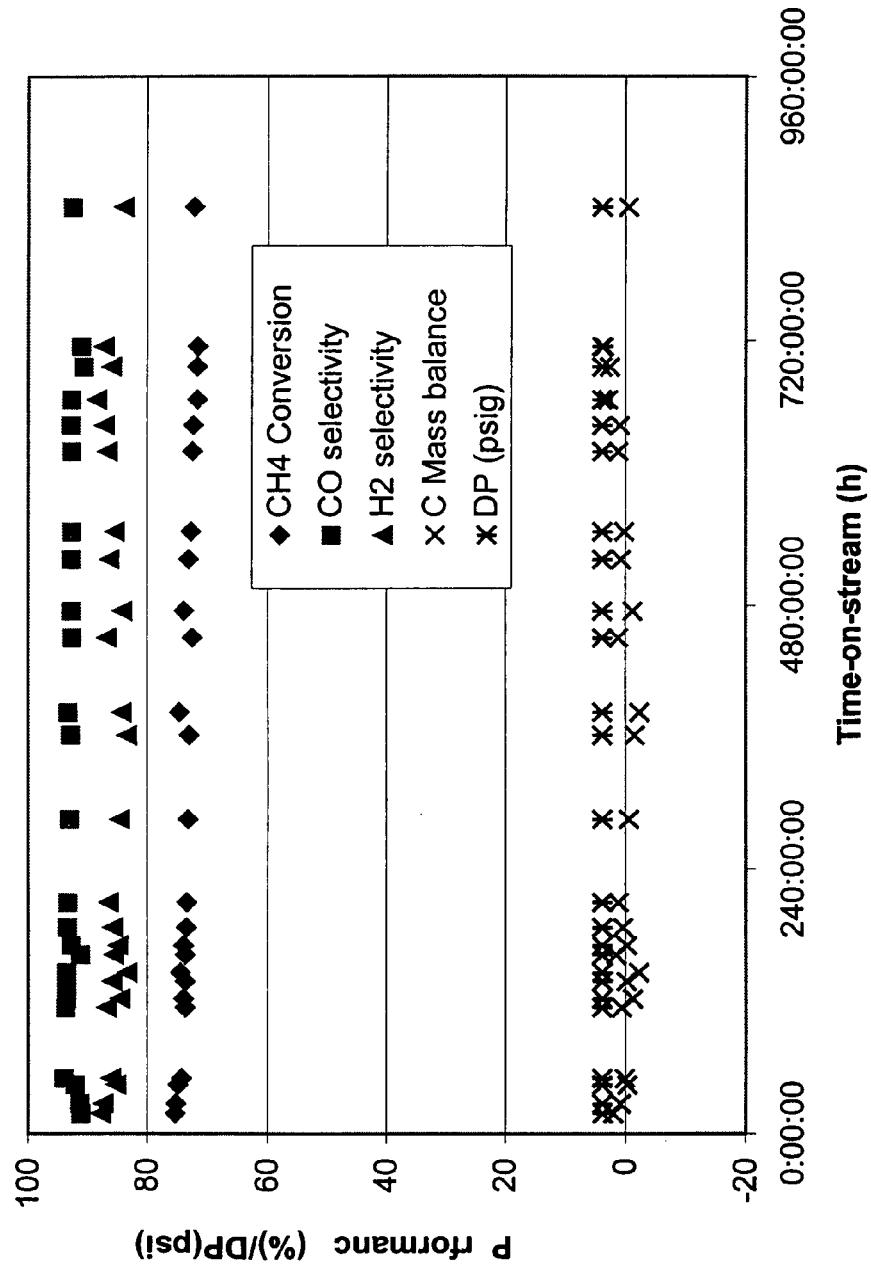
FIG. 9 is a plot of process performance versus time for the tests disclosed in Example 7.

The resulting fin supported catalyst is tested for partial oxidation of methane to CO and $H_2$ at 1 atmosphere using the pellet described in Example 3. The pellet is placed in a furnace. The catalyst is reduced with $H_2$ at 450° C. for 30 min before use. The feed gas composition contains 29.6% of $CH_4$ and 70.4% of air ($CH_4/O_2=2/1$), with 2030 ml/min of total flow rate (standard conditions). The temperature of the furnace is adjusted to keep the pellet skin temperature at mid-length at 850° C. The temperature of the feed stream at the inlet of the furnace is at room temperature. The feed stream is preheated before entering the pellet. The length of tubing from the entrance of furnace to the pellet is ten feet. The outlet pressure of the product stream is atmospheric pressure. The contact time is 3.3 ms. The pressure drop in the pellet, which is measured by capsuhelic differential pressure gauge, is 3.7 psi. The composition of product is analyzed with two-column Gas Chromatograph. The performance of the fin is measured in terms of $CH_4$ conversion, $H_2$ selectivity and CO selectivity. The results are shown in FIG. 9.

The test results indicate that this catalyst is stable. As shown in FIG. 9, $CH_4$ conversion, CO selectivity and $H_2$ selectivity are substantially unchanged during 840 hours time-on-stream.

EXAMPLE 8

Figure 10:
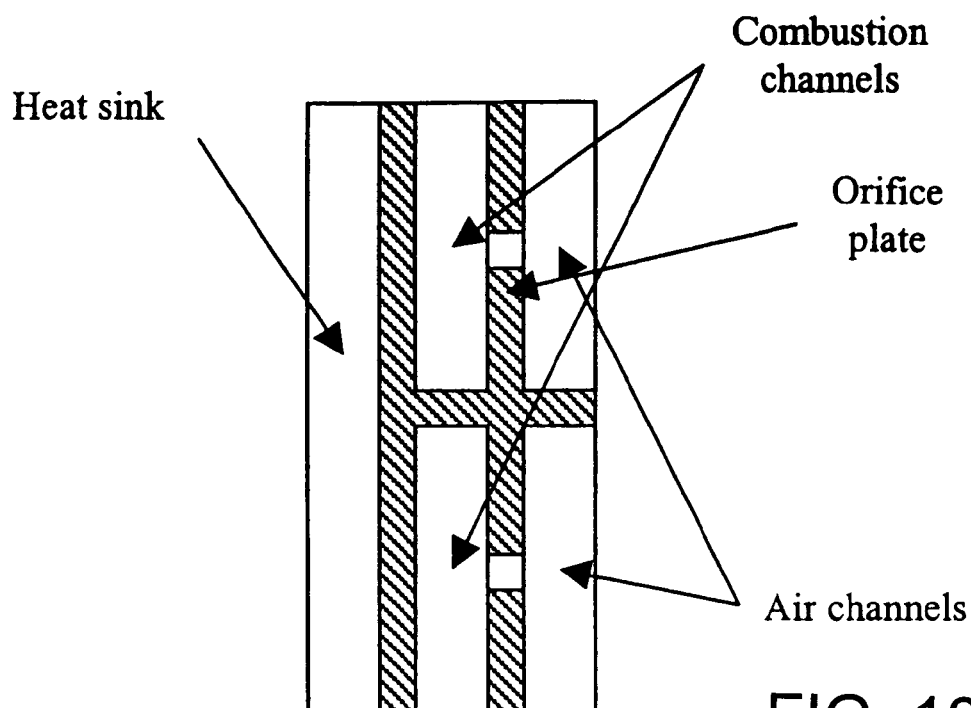
FIG. 10 illustrates the channel arrangement for the microchannel reactor used in the tests disclosed in Example 8.

A welded Inconel reactor is fabricated to test methane combustion performance. The reactor includes two parallel channels for the combustion. Each channel is 0.160" wide and 0.025" tall. The length of reactor is 7.00". The channels are separated by 0.060" rib between them. On one side of the combustion channels, an identical pair of channels (referred as air channels) is placed to flow air required for combustion of fuel. The combustion and air channels are separated by an orifice plate with 12 circular orifices (0.012" diameter) spaced along the reactor length to distribute air into the fuel. The orifices are non-uniformly spaced to distribute air in the combustion channel. The first orifice is placed at the beginning of the reactor. The subsequent orifices are placed at distances of 0.252", 0.555", 0.905", 1.304", 1.751", 2.248", 2.794", 3.393", 4.047", 4.760", and 5.528" from the first orifice. On the other side of the combustion channel, a single heat exchange channel is placed to carry fluid which acts as a sink for combustion heat. The channel is 0.380" wide and 0.012" tall. The length of the channel is the same as the combustion channel length. The arrangement of different channels is shown in FIG. 10.

The combustion channels are coated with a combustion catalyst with solution coating. The device is first calcined in air at 1000° C. for 1 hour to generate a chromia layer on the surface. The heating and cooling rate is 3.5° C./min. Subsequently, a solution containing 5.7 wt. % of $Pd(NO_3)_2$ and 43 wt. % of $Ce(NO_3)_3.6H_2O$ is doped onto the channels. The excess solution is blown out by compressed air. The coated channels are then dried at 100° C. for 1 hour. The Pd coating process is repeated twice. The coated channels are then calcined in air at 850° C. for 1 hour.

The fuel used for the combustion is methane. The total flow rate of methane in the combustion channels is 1.0 standard liters per minute (SLPM). The total air flow rate in the air channels is 11.5 SLPM. The air is preheated to reactor temperature before mixing it in fuel. The heat sink is provided by a steam methane reforming reaction. The sink channel (referred as SMR channel) is coated with a steam methane reforming (SMR) catalyst. A mixture of 1.09 SLPM and 2.63 cc of watervapors are flowed through SMR channel. The inlet temperature of flow in SMR channel is between 800° C. and 850° C. The average temperature of the combustion channel is between 850° C. and 925° C. Based on the volume of combustion channel, the contact time is 4.4 ms. The methane conversion in the combustion channel is calculated as:

$$CH_4 \text{ Conversion } (\%) = (V_{CH4, \text{in}} - V_{CH4, \text{out}})/(V_{CH4, \text{in}}) \times 100$$

For the combustion catalyst, the methane conversion is 30.6% at an average temperature of 862° C. For this device an average of 9.3 W/cm² is transferred to the SMR reaction. The pressure drop in the combustion channel is between 2.5 and 5.0 psi.

EXAMPLE 9

Figure 11:
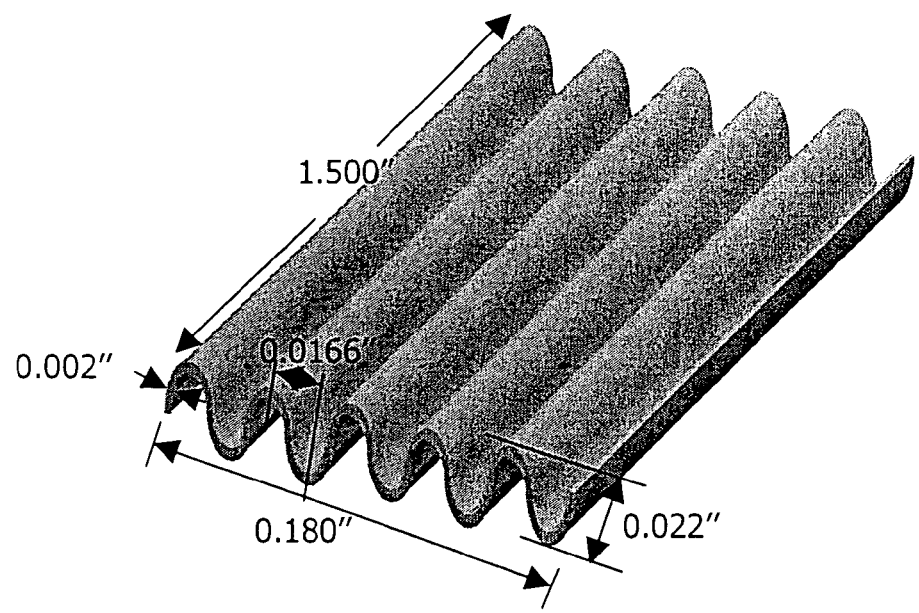
FIG. 11 illustrates the fin assembly for the microchannel reactor used in Example 9.

Another Inconel reactor device is fabricated to test combustion performance using a supported partial oxidation catalyst. The device has same combustion and air channel dimensions as microchannel reactor used in Example 8 except for the total partial oxidation and combustion channel length. A serrated metal sheet is used as a fin as shown in FIG. 11. Two fins are introduced at the beginning of the two partial oxidation and combustion channels. The total length of the partial oxidation and combustion channel is 8.5" to accommodate the fin, where the fin is 1.5" long and the subsequent combustion channel is 7" long. The fin is made of FeCrAlY. The dimensions of the fin are summarized in the table below.

|  | Dimensions |
| --- | --- |
| Overall Length | 1.500" |
| Overall width | 0.180" |
| Overall height | 0.022" |
| Fin thickness | 0.002" |
| Fins per inch | 60 |

The fins are coated with a partial oxidation catalyst to convert methane to CO and $H_2$ before combustion. The fins are cleaned in iso-propanol for 20 min with sonication. After drying at 100° C. for 1 hour and cooling to room temperature, the fins are cleaned in 20 wt. % $HNO_3$ solution for 20 min with sonication. The fins are then rinsed with deionized water until pH value is 7. After drying at 120° C. for 1 hour, the fins are heated to 1000° C. in air at a heating rate of 3.5° C./min and calcined at 1000° C. for 8 h in air. A dense $Al_2O_3$ layer is generated after the calcination and the $Al_2O_3$ layer-functions as a protection scale and also improves the adhesion between the coating and the fins. Also, an $Al_2O_3$ and $ZrO_2$ containing slurry is prepared for coating. 10 g $ZrO_2$ powder, 55 g of deionized $H_2O$, 1.2 ml of concentrated nitric acid and 200 g $Al_2O_3$ beads with 3 mm diameter are mixed in a container. The mixture is then ball-milled for 2 days. After that, 2.0 g of $ZrO_2$ slurry, 0.54 g of gamma-$Al_2O_3$ powder, 0.46 g of $La(NO_3)_3 \cdot 6H_2O$ and 0.5 g of $H_2O$ are mixed with stirring. The $Al_2O_3$, which is acidic gamma $Al_2O_3$, is ground to a powder smaller than 53 microns. Subsequently, the above $Al_2O_3$—$ZrO_2$ slurry is washcoated onto the fins by dipping. The slurry-coated fins are dried at 120° C. for 1 hour and then calcined at 1000° C. for 1 hour at a heating and cooling rate of 3.5° C./min. The slurry loading is 6.4 mg per fin. After that, 10 wt. % $Rh(NO_3)_3$ solution is dropped onto the fins and the excess solution is blown out by compressed air. Finally the slurry-coated catalysts are dried at 120° C. for 1 hour and then calcined at 500° C. for 1 hour in air. The Rh loading is around 0.6 mg per fin.

In the combustion channels, the orifice plate for distributing air into the fuel is modified by increasing the number of orifices to 17 and introducing non-circular orifices. The first orifice is placed in the combustion channel at a distance between 0.01" and 0.20" after the partial oxidation zone. The first orifice consists of rectangular slots with semi-circular ends of diameter 0.012". The longest length of the slot is in the direction of flow. The second orifice is equilateral triangular in shape with 0.012" side length and is placed at a distance of 0.133" from first orifice. The third & fourth orifices are of 0.012" diameter holes placed 0.267" from first orifice. The fifth orifice is again a triangular slot placed 0.386" from the first orifice. Orifice six to fifteen are circular holes with diameter 0.012" and are placed at 0.594", 0.769", 0.969", 1.168", 1.615", 2.112", 2.658", 3.257", 3.257", 3.857", 4.624" from the first orifice. Orifice sixteen and seventeen are 0.012" diameter holes place 5.392" from first orifice. This pattern of orifices provides an ideal oxygen equivalence ratio of 0.5, defined as:

$$\xi_{O2} = \frac{Y_{O2}}{Y_{O2} + Y_{O2,stoic}}$$

Where $Y_{O2}$ is the mole fraction of oxygen and $Y_{O2,stoic}$ is stoichiometric oxygen mole fraction necessary for complete combustion.

The combustion channels are coated with combustion catalyst. The device is first calcined in air at 1000° C. for 3 h to generate a chromia layer on the surface. The heating and cooling rate is 3.5° C./min. 10 wt. % $Rh(NO_3)_3$ solution is then dropped onto the combustion channels and the excess solution is blown out by compressed air. After drying at 100° C. for 1 hour, the coated channels are calcined at 800° C. for 1 hour in air. Subsequently, a solution containing 5.7 wt. % of $Pd(NO_3)_2$ and 43 wt. % of $Ce(NO_3)_3 \cdot 6H_2O$ is doped onto the channels. The excess solution is blown out by compressed air. The coated channels are then dried at 100° C. for 1 hour. The Pd coating process is repeated once. The coated channels are then calcined at 1000° C. for 1 h. Finally, 10 wt. % $Pt(NH_3)_4(NO_3)_2$ solution is dropped onto the channels. After drying at 100° C. for 1 hour, the coated channels are calcined at 900° C. for 1 hour in air.

The reactor performance with integrated partial oxidation and combustion reaction is tested. The total flow rate of methane in the two combustion channels is 1.33 SLPM. The methane is premixed with air to have $CH_4:O_2$ ratio of 2:1 in the partial oxidation channels. The total flow rate of air in the air channels is 10.9 SLPM. The air is preheated to the reactor temperature before mixing into fuel. The heat sink is provided by a steam methane reforming reaction. The sink channel (referred as SMR channel) is coated with steam methane reforming (SMR) catalyst. A mixture of 2.18 SLPM and 5.27 cc of water vapors flow through the SMR channel. The inlet temperature of flow in SMR channel is between 800° C. and 850° C. The average partial oxidation zone temperature is between 750° C. and 800° C. and average combustion zone temperature is between 850° C. and 925° C. Based on the volume of combustion channels, the contact time in combustion channels is 4.5 ms. The total $CH_4$ conversion is 92.2%, an increase of 61.6% as compared to that without partial oxidation catalyst. This demonstrates that partial oxidation assists methane combustion significantly. For this device an average of 18.8 W/cm$^2$ is transferred to the SMR reaction. The pressure drop in the combustion channel is between 2.5 and 5.0 psi.

While the invention has been explained in relation to various detailed embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A process for converting a hydrocarbon reactant to a partial oxidation reaction product comprising CO and $H_2$ in a microchannel reactor, the microchannel reactor comprising at least one process microchannel and at least one partial oxidation reaction catalyst in the at least one process microchannel, the process comprising:

(A) mixing a reactant composition comprising the hydrocarbon reactant and oxygen or a source of oxygen in the at least one process microchannel and flowing the resulting mixture in the at least one process microchannel in contact with the at least one partial oxidation reaction catalyst under partial oxidation reaction conditions to form the product, the hydrocarbon reactant comprising methane, the contact time for the reactant composition within the at least one process microchannel being up to about 500 milliseconds, the temperature of the reactant composition and product within the at least one process microchannel being up to about 1500° C., the conversion of the hydrocarbon reactant being at least about 50%.

2. The process of claim 1 wherein the product formed in step (A) is an intermediate product, the process further comprising the following additional step subsequent to step (A):

(B) flowing the intermediate product formed in step (A) through a microchannel reactor in contact with a combustion catalyst under reaction conditions to form a final product comprising $CO_2$ and $H_2O$.

3. The process of claim 1 wherein the reactant composition further comprises $H_2O$ and the product comprises $H_2$, CO and $CO_2$.

4. The process of claim 1 wherein the reactant composition is preheated prior to step (A).

5. The process of claim 1 wherein the reactant composition and oxygen or oxygen source are mixed prior to step (A).

6. The process of claim 1 wherein the reactant composition and oxygen or oxygen source are mixed during step (A).

7. The process of claim 1 wherein the microchannel reactor comprises a plurality of process microchannels containing the catalyst, a header providing a flow passageway for fluid to enter the process microchannels, and a footer providing a flow passageway for fluid to leave the process microchannels.

8. The process of claim 7 wherein each process microchannel has an internal dimension of width or height of up to about 10 mm.

9. The process of claim 7 wherein each of the process microchannels has an entrance, an exit and an elongated section extending between the entrance and the exit, the process microchannels further comprising at least one additional entrance in the elongated section, at least one reactant entering the process microchannels through the at least one additional entrance.

10. The process of claim 7 wherein the process microchannels are made of a material comprising: steel; monel; inconel; aluminum; titanium; nickel: copper; brass; an alloy of any of the foregoing metals; a polymer; ceramics; glass; a composite comprising a polymer and fiberglass; quarlz; silicon; or a combination of two or more thereof.

11. The process of claim 7 wherein the microchannel reactor further comprises heat exchange channels in thermal contact with the process microchannels.

12. The process of claim 11 wherein the heat exchange channels comprise microchannels.

13. The process of claim 11 wherein each heat exchange channel has an internal dimension of width or height of up to about 10 mm.

14. The process of claim 11 wherein the heat exchange channels are made of a material comprising: steel; monel; inconel; aluminum; titanium; nickel; copper; brass; an alloy of any of the foregoing metals; a polymer, ceramics: glass; a composite comprising polymer and fiberglass; quartz; silicon; or a combination of two or more thereof.

15. The process of claim 9 wherein the at least one reactant entering the process microchannels through the at least one additional entrance comprises the oxygen or source of oxygen.

16. The process of claim 1 wherein the hydrocarbon reactant further comprises: an aliphatic compound, an aromatic compound, or a mixture thereof.

17. The process of claim 1 wherein the hydrocarbon reactant further comprises an alkane containing 2 to about 20 carbon atoms per molecule.

18. The process of claim 1 wherein the hydrocarbon reactant further comprises ethane, propane, isopropane, butane, isobutane, a pentane, a hexane, a heptane, an octane, a nonane, a decane, or a mixture of two or more thereof.

19. The process of claim 1 wherein the hydrocarbon reactant comprises natural gas.

20. The process of claim 1 wherein the hydrocarbon reactant further comprises an alkene containing 2 to about 20 carbon atoms.

21. The process of claim 1 wherein the hydrocarbon reactant further comprises ethylene; propylene; 1-butane; 2-butene; isobutylene; 1-pentene; 2-pentene; 3-methyl-1-butene: 2-methyl-2-butene; 1-hexene; 2,3-dimethyl-2-butene; 1-heptene; 1-octene; 1-nonene; 1-decene; or a mixture of two or more thereof.

22. The process of claim 1 wherein the hydrocarbon reactant further comprises a polyene containing 3 to about 20 carbon atoms.

23. The process of claim 1 wherein the hydrocarbon reactant further comprises 1,2-propadiene; 1,3-butadiene; 2-methyl-1,3-butadiene; 1,3-pentadiene; 1,4-pentadiene; 1,5-hexadiene; 2,4-hexadiene; 2,3-dimethyl-1,3-butadiene; or a mixture of two or more thereof.

24. The process of claim 1 wherein the hydrocarbon reactant further comprises an alkyl or alkylene substituted aromatic compound.

25. The process of claim 1 wherein the hydrocarbon reactant comprises toluene, o-xylene, m-xylene, p-xylene, hemimellitene, pseudocumene, mesitylene, prehnitene, isodurene, durene, pentamethylbenzene, hexamethylbenzene, ethylbenzene, n-propylbenzene, cumene, n-butylbenzene, isobutylbenzene, sec-butylbenzene, tert-butylbenzene, p-cymene, styrene, or a mixture of two or more thereof.

26. The process of claim 1 wherein the hydrocarbon reactant further comprises a natural oil, synthetic oil, or mixture thereof.

27. The process of claim 1 wherein the hydrocarbon reactant further comprises a distillate fuel.

28. The process of claim 1 wherein the hydrocarbon reactant further comprises naphtha, diesel fuel, fuel oil, kerosene or gasoline.

29. The process of claim 1 wherein the hydrocarbon reactant further comprises a hydrocarbon derived from a vegetable source, a mineral source, or mixture thereof.

30. The process of claim 1 wherein the hydrocarbon reactant further comprises a hydrocarbon derived from soybean, rapeseed, palm, shale, coal, tar sands, or a mixture of two or more thereof.

31. The process of claim 1 wherein the source of oxygen comprises air.

32. The process of claim 1 wherein the reactant composition further comprises a diluent material.

33. The process of claim 11 wherein the process microchannels exchange heat with a heat exchange fluid flowing through the heat exchange channels.

34. The process of claim 33 wherein the heat exchange fluid undergoes a phase change as it flows through the heat exchange channels.

35. The process of claim 11 wherein the process microchannels are cooled by an endothermic chemical reaction conducted in the heat exchange channels.

36. The process of claim 35 wherein the endothermic chemical reaction comprises a steam reforming reaction or a dehydrogenation reaction.

37. The process of claim 11 wherein the reactant composition flows through the process microchannels in a first direction, and a heat exchange fluid flows through the heat exchange channels in a second direction, the second direction being cross current relative to the first direction.

38. The process of claim 11 wherein the reactant composition flows through the process microchannels flow in a first direction, and a heat exchange fluid flows through the heat exchange channels in a second direction, the second direction being cocurrent relative to the first direction.

39. The process of claim 11 wherein the hydrocarbon reactant composition flows through the process microchannels in a first direction, and a heat exchange fluid flows Through the heat exchange channels in a second direction, the second direction being counter current relative to the first direction.

40. The process of claim 11 wherein a heat exchange fluid flows through the heat exchange channels, the heat exchange fluid comprising air, steam, liquid water, carbon dioxide, gaseous nitrogen, liquid nitrogen, a gaseous hydrocarbon or a liquid hydrocarbon.

41. The process of claim 1 wherein the catalyst is in the form of particulate solids.

42. The process of claim 1 wherein the catalyst is supported by a support structure made of a material comprising an alloy comprising Ni, Cr and Fe, or an alloy comprising Fe, Cr, Al and Y.

43. The process of claim 1 wherein the catalyst is supported on a support structure having a flow-by configuration, a flow-through configuration, or a serpentine configuration.

44. The process of claim 1 wherein the catalyst is supported on a support structure having the configuration of a foam, felt, wad, fin, or a combination of two or more thereof.

45. The process of claim 1 wherein the catalyst is supported on a support structure having a flow-by configuration with an adjacent gap, a foam configuration with an adjacent gap, a fin structure with gaps, a washcoat on a substrate, or a gauze configuration with a gap for flow.

46. The process of claim 1 wherein the catalyst is supported on a support structure in the form of a fin assembly comprising at least one fin.

47. The process of claim 46 wherein the fin assembly comprises a plurality of parallel spaced fins.

48. The process of claim 46 wherein the fin has an exterior surface and a porous material overlies at least part of the exterior surface of the fin, the catalyst being supported by the porous material.

49. The process of claim 48 wherein the porous material comprises a costing, fibers, foam or felt.

50. The process of claim 46 wherein the fin has an exterior surface and a plurality fibers or protrusions extend from at least part of the exterior surface of the fin, the catalyst being supported by the protrusions.

51. The process of claim 46 wherein the fin has an exterior surface and the catalyst is: washcoated on at least part of the exterior surface of the fin; grown on at least part of the exterior surface of the fin from solution; or deposited on at least part of the exterior surface of the fin using vapor deposition.

52. The process of claim 46 wherein the fin assembly comprises a plurality of parallel spaced fins, at least one of the fins having a length that is different than the length of the other fins.

53. The process of claim 46 wherein the fin assembly comprises a plurality of parallel spaced fins, at least one of the fins having a height that is different than the height of the other fins.

54. The process of claim 46 wherein the fin has a cross section having the shape of a square or a rectangle.

55. The process of claim 46 wherein the fin has a cross section having the shape of a trapezoid.

56. The process of claim 46 wherein the fin is made of a material comprising: steel; aluminum; titanium; iron; nickel; platinum; rhodium; copper chromium; brass; an alloy of any of the foregoing metals; a polymer; ceramics; glass; a composite comprising polymer and fiberglass; quartz; silicon; or a combination of two or more thereof.

57. The process of claim 46 wherein the fin is made of an alloy comprising Ni, Cr and Fe, or an alloy comprising Fe, Cr, Al and Y.

58. The process of claim 46 wherein the fin is made of $Al_2O_3$ forming material.

59. The process of claim 46 wherein the fin is made of a $Cr_2O_3$ forming material.

60. The process of claim 1 wherein the catalyst comprises Rh, Pt, Ni, Cr, Ru, Pd, Os, Ir, or an oxide thereof, or a mixture of two or more thereof.

61. The process of claim 1 wherein the catalyst comprises a composition represented by the formula $$M^1_a M^2_b M^3_c Al_d O_x$$

wherein
$M^1$ is Rh, Ni, Pd, Pt, Ru, Co or a mixture of two or more thereof;
$M^2$ is Ce, Pr, Tb or a mixture of two or more thereof;
$M^3$ is La, Ba, Zr, Mg, Ca or a mixture of two or more thereof;
a is a number In the range of about 0.0001 to about 1;
b is a number in the range of zero to about 0.9999;
c is a number in the range of about 0.0001 to about 0.9999;
d is a number in the range of about 0.0001 to about 0.9999; and
x is the number of oxygens needed to fulfill the valency requirements of the elements present;
the catalyst being coated on an interior wall of the process microchannel, or supported on a foam, felt, wad or fin positioned within the process microchannel.

62. The process of claim 2 wherein the combustion catalyst comprises a noble metal or an oxide thereof, a pervoskite or an aluminate.

63. The process of claim 62 wherein the combustion catalyst further comprises Ce, Tb or Pr, or an oxide thereof, or a mixture of two or more thereof.

64. The process of claim 2 wherein the combustion catalyst comprises Pt, Rh, Pd, Co. Mn, Fe, Ni, or an oxide thereof, or a mixture of two or more thereof.

65. The process of claim 1 wherein the contact time of the reactant composition and/or product with the catalyst is from about 0.1 milliseconds to about 100 seconds.

66. The process of claim 1 wherein the temperature of the reactant composition entering the process microchannel is in the range of about 200° C. to about 1000° C.

67. The process of claim 1 wherein the pressure of the reactant composition entering the process microchannel is in the range of about 0.1 to about 100 atmospheres.

68. The process of claim 1 wherein the space velocity for the flow of the reactant composition and product through the process microchannel is at least about 100 $hr^{-1}$.

69. The process of claim 1 wherein the pressure drop for the flow of the reactant composition and product through the process microchannel is up to about 2 atmospheres per meter of length of the process microchannel.

70. The process of claim 11 wherein a heat exchange fluid flows through the heat exchange channels, the total pressure drop for the heat exchange fluid flowing through the heat exchange channels being up to about 10 atmospheres.

71. A process for converting a hydrocarbon reactant to a partial oxidation reaction product comprising $H_2$ and CO, the process comprising:

(A) flowing a reactant composition comprising the hydrocarbon reactant and oxygen or a source of oxygen in a microchannel reactor in contact with a partial oxidation reaction catalyst under partial oxidation reaction conditions to convert the reactant composition to the product, the hydrocarbon reactant comprising methane, the microchannel reactor comprising at least one process microchannel, the catalyst being in the process microchannel, the partial oxidation reaction catalyst comprising a composition represented by the formula $$M^1_a M^2_b M^3_c Al_d O_x$$

wherein
- $M^1$ is Rh, Ni, Pd, Pt, Ru, Co or a mixture of two or more thereof;
- $M^2$ is Ce, Pr, Tb or a mixture of two or more thereof;
- $M^3$ is La, Ba, Zr, Mg, Ca or a mixture of two or more thereof;
- a is a number in the range of about 0.0001 to about 1;
- b is a number in the range of zero to about 0.9999;
- c is a number in the range of about 0.0001 to about 0.9999;
- d is a number in the range of about 0.0001 to about 0.9999; and
- x is the number of oxygens needed to fulfill the valency requirements of the elements present;

the catalyst being coated on an interior wall of the process microchannel, or supported on a foam, felt, wad or fin positioned within the process microchannel.

72. The process of claim 1 wherein the catalyst is represented by the formula $Rh/LaAl_{11}O_{18}$ or $Rh/LaAlO_3$.

73. A process for converting a hydrocarbon reactant to a partial oxidation reaction product comprising CO and $H_2$, comprising:
flowing a reactant composition comprising the hydrocarbon reactant and oxygen or a source of oxygen in a microchannel reactor in contact with a partial oxidation reaction catalyst under partial oxidation reaction conditions to form the product, the microchannel reactor comprising at least one process microchannel, the catalyst being in the at least one process microchannel, the hydrocarbon reactant comprising methane and at least one additional hydrocarbon capable of undergoing an oxidation reaction, the contact time for the reactant composition within the process microchannel being up to about 500 milliseconds, the temperature of the reactant composition and product within the process microchannel being up to about 1150° C., the conversion of the hydrocarbon reactant being at least about 50%.

74. A process for converting a hydrocarbon reactant to a partial oxidation reaction product comprising CO and $H_2$, comprising:
flowing a reactant composition comprising the hydrocarbon reactant and oxygen or a source of oxygen in a microchannel reactor in contact with a partial oxidation reaction catalyst under partial oxidation reaction conditions to form the product, the microchannel reactor comprising at least one process microchannel, the catalyst being in the at least one process microchannel, the at least one process microchannel exchanging heat with a heat exchange fluid in at least one heat exchange channel, the at least one heat exchange channel being in thermal contact with the at least one process microchannel, the heat exchange fluid undergoing a phase change in the at least one heat exchange channel, the hydrocarbon reactant comprising methane, the contact time for the reactant composition in the at least one process microchannel being up to about 500 milliseconds, the temperature of the reactant composition and product in the at least one process microchannel being up to about 1150° C., the conversion of the hydrocarbon reactant being at least about 50%.

75. A process for converting a hydrocarbon reactant to a partial oxidation reaction product comprising CO and $H_2$ in a microchannel reactor, comprising:
mixing a reactant composition comprising the hydrocarbon reactant and oxygen or a source of oxygen in at least one process microchannel and flowing the mixture into a process microchannel in contact with a partial oxidation reaction catalyst under partial oxidation reaction conditions to form the product, the microchannel reactor comprising at least one process microchannel, the catalyst being in the process microchannel, the at least one process microchannel exchanging heat with a heat exchange fluid in at least one heat exchange channel, the at least one heat exchange channel being in thermal contact with the at least one process microchannel, an endothermic reaction being conducted in the at least one heat exchange channel, the hydrocarbon reactant comprising methane, the contact time for the reactant composition in the at least one process microchannel being up to about 500 milliseconds, The temperature of the reactant composition and product in the at least one process microchannel being up to about 1150° C., the conversion of the hydrocarbon reactant being at least about 50%.

76. A process for converting a hydrocarbon reactant to a partial oxidation reaction product comprising CO and $H_2$, comprising:
flowing a reactant composition comprising the hydrocarbon reactant and oxygen or a source of oxygen in a microchannel reactor in contact with a partial oxidation reaction catalyst under partial oxidation reaction conditions to form the product, the microchannel reactor comprising at least one process microchannel, the catalyst being in the at least one process microchannel, the catalyst comprising $Rh/LaAl_{11}O_{18}$ or $Rh/LaAlO_3$, the hydrocarbon reactant comprising methane, the contact time for the reactant composition in the at least one process microchannel being up to about 500 milliseconds, the temperature of the reactant composition and product in the at least one process microchannel being up to about 1150° C., the conversion of the hydrocarbon reactant being at least about 50%.

* * * * *